US012788797B2

(12) United States Patent
Hamilton et al.

(10) Patent No.: US 12,788,797 B2
(45) **Date of Patent: *Nov. 10, 2026**

(54) METHODS FOR PREVENTING OR TREATING ALLERGY BY ADMINISTERING AN IL-4R ANTAGONIST

(71) Applicants: REGENERON PHARMACEUTICALS, INC., Tarrytown, NY (US); SANOFI BIOTECHNOLOGY, Paris (FR)

(72) Inventors: Jennifer D. Hamilton, Ridgefield, CT (US); Brian N. Swanson, Paris (FR)

(73) Assignees: REGENERON PHARMACEUTICALS, INC., Tarrytown, NY (US); SANOFI BIOTECHNOLOGY, Paris (FR)

( * ) Notice: Subject to any disclaimer, the term of this patent is extended or adjusted under 35 U.S.C. 154(b) by 221 days.

This patent is subject to a terminal disclaimer.

(21) Appl. No.: 18/452,155

(22) Filed: Aug. 18, 2023

(65) Prior Publication Data

US 2024/0082353 A1 Mar. 14, 2024

Related U.S. Application Data

(63) Continuation of application No. 16/329,184, filed as application No. PCT/US2017/049538 on Aug. 31, 2017, now Pat. No. 11,771,743.

(60) Provisional application No. 62/382,501, filed on Sep. 1, 2016, provisional application No. 62/425,726, filed on Nov. 23, 2016.

(51) Int. Cl.

| | |
|---|---|
| ***A61K 38/17*** | (2006.01) |
| ***A61K 9/00*** | (2006.01) |
| ***A61K 39/00*** | (2006.01) |
| ***A61P 17/00*** | (2006.01) |
| ***A61P 37/08*** | (2006.01) |
| ***C07K 16/28*** | (2006.01) |
| ***G01N 33/569*** | (2006.01) |
| *A61K 45/06* | (2006.01) |

(52) U.S. Cl.

CPC ........ *A61K 38/1774* (2013.01); *A61K 9/0019* (2013.01); *A61K 39/00* (2013.01); *A61P 17/00* (2018.01); *A61P 37/08* (2018.01); *C07K 16/2866* (2013.01); *G01N 33/56966* (2013.01); *A61K 2039/505* (2013.01); *A61K 2039/545* (2013.01); *A61K 45/06* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 5,599,905 | A | 2/1997 | Mosley |
| 5,714,146 | A | 2/1998 | Lewis |
| 5,717,072 | A | 2/1998 | Mosley |
| 5,856,296 | A | 1/1999 | Mosley |
| 5,985,280 | A | 11/1999 | Ritter |
| 6,156,877 | A | 12/2000 | Ritter |
| 6,391,581 | B1 | 5/2002 | Mosley |
| 6,548,655 | B1 | 4/2003 | Mosley |
| 6,716,587 | B2 | 4/2004 | Mosley |
| 7,141,653 | B2 | 11/2006 | Greenfeder |
| 7,186,809 | B2 | 3/2007 | Pluenneke |
| 7,317,090 | B2 | 1/2008 | Mosley |
| 7,422,742 | B2 | 9/2008 | Greenfeder |
| 7,531,169 | B2 | 5/2009 | Singh |
| 7,605,237 | B2 | 10/2009 | Stevens |
| 7,608,693 | B2 | 10/2009 | Martin |
| 7,615,213 | B2 | 11/2009 | Kasaian et al. |
| 7,794,717 | B2 | 9/2010 | Stevens |
| 8,030,003 | B2 | 10/2011 | Rothenberg |
| 8,075,887 | B2 | 12/2011 | Martin |
| 8,075,897 | B2 | 12/2011 | Spertini |
| 8,092,802 | B2 | 1/2012 | Stevens |
| 8,092,804 | B2 | 1/2012 | Eriksson |
| 8,252,284 | B2 | 8/2012 | Singh |
| 8,324,192 | B2 | 12/2012 | Dohil |
| 8,337,839 | B2 | 12/2012 | Martin |
| 8,338,135 | B2 | 12/2012 | Stevens |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Wachholz et al., J Immunotoxicol. Jul. 1, 2005;1(3):189-99. doi: 10.1080/15476910490919140. PMID: 18958652.*

(Continued)

*Primary Examiner* — Michael Szperka

(74) *Attorney, Agent, or Firm* — Schwabe, Williamson & Wyatt PC; Lisa Dornbach Flanagan

(57) ABSTRACT

The present invention provides methods for preventing or treating allergy. Also provided are methods for reducing the susceptibility to an allergen in a subject in need thereof. In certain embodiments, the subject has a disease or disorder selected from the group consisting of atopic dermatitis, asthma, allergic rhinitis, and eosinophilic esophagitis. The methods of the present invention comprise administering to a subject in need thereof a pharmaceutical composition comprising an interleukin-4 receptor (IL-4R) antagonist such as an anti-IL-4R antibody.

18 Claims, 11 Drawing Sheets

Specification includes a Sequence Listing.

(56) References Cited

U.S. PATENT DOCUMENTS 8,497,528 B2 7/2013 Lee
8,604,171 B2 12/2013 Singh
8,637,239 B2 1/2014 Furuta
8,735,095 B2 5/2014 Martin et al.
8,945,559 B2 2/2015 Dix
9,238,692 B2 1/2016 Dix
9,290,574 B2 * 3/2016 Kostic ....................... A61P 1/12
9,334,331 B2 5/2016 Igawa et al.
9,415,015 B2 8/2016 Jacobi et al.
9,574,004 B2 2/2017 Ardeleanu
10,059,771 B2 8/2018 Mannent
10,066,017 B2 9/2018 Mannent
10,137,139 B2 * 11/2018 Tabuteau ............. A61K 9/0056
10,137,193 B2 * 11/2018 Pirozzi ............... C07K 16/2866
10,370,449 B2 8/2019 Graham
10,392,439 B2 * 8/2019 Stahl .................. C07K 16/2866
10,421,807 B2 9/2019 Gonzales et al.
10,435,473 B2 10/2019 Dix
10,485,844 B2 * 11/2019 Radin ..................... A61P 17/00
10,669,341 B2 * 6/2020 Stahl .................. C07K 16/2866
10,676,530 B2 6/2020 Stahl
10,730,948 B2 8/2020 Kostic
11,034,768 B2 * 6/2021 Amin ..................... A61B 5/445
11,053,309 B2 * 7/2021 Radin ................ A61K 39/3955
11,771,743 B2 * 10/2023 Hamilton ........... C07K 16/2866
424/275.1
12,090,201 B2 * 9/2024 Bansal ................. A61K 9/0019
2003/0103938 A1 6/2003 Jinquan
2003/0113387 A1 6/2003 Tsuchida
2003/0124121 A1 7/2003 Pluenneke
2005/0031609 A1 2/2005 Hultsch
2005/0074462 A1 4/2005 Holmgren
2005/0118176 A1 6/2005 Mosley
2005/0255532 A1 11/2005 Ruben
2005/0282181 A1 12/2005 Yan
2006/0013811 A1 1/2006 Dina
2007/0041976 A1 2/2007 Pluenneke
2007/0274996 A1 11/2007 Carter
2008/0054606 A1 3/2008 Mitsuo et al.
2008/0160035 A1 7/2008 Stevens et al.
2009/0074793 A1 3/2009 Martin
2009/0098142 A1 4/2009 Kasaian
2009/0264392 A1 10/2009 Warndahl
2010/0021476 A1 1/2010 Stevens et al.
2010/0047254 A1 2/2010 Martin
2010/0291107 A1 11/2010 Stevens et al.
2011/0195500 A1 8/2011 Rothenberg
2012/0004205 A1 1/2012 Rothenberg
2012/0052072 A1 3/2012 Martin
2012/0097565 A1 4/2012 Dix
2012/0135010 A1 5/2012 Stevens et al.
2012/0164080 A1 6/2012 Hill
2012/0207815 A1 8/2012 Benhamou
2013/0052190 A1 2/2013 Collins
2013/0078675 A1 3/2013 Martin
2013/0324435 A1 12/2013 Rothenberg
2014/0072583 A1 * 3/2014 Ardeleanu ........... A61K 31/573
424/172.1
2014/0187523 A1 7/2014 Dohil
2014/0271681 A1 9/2014 Martin
2014/0356372 A1 * 12/2014 Stahl .................. C07K 16/2866
424/142.1
2015/0017176 A1 1/2015 Kostic
2015/0185228 A1 7/2015 Reisacher
2015/0246973 A1 9/2015 Graham
2016/0152718 A1 6/2016 Kostic
2016/0185866 A1 6/2016 Mannent
2017/0333557 A1 11/2017 Ardeleanu
2018/0078603 A1 3/2018 Radin
2018/0094069 A1 4/2018 Stahl
2018/0094070 A1 4/2018 Stahl
2018/0169220 A1 6/2018 Euverink et al.
2018/0179288 A1 6/2018 Martin et al.
2019/0040126 A1 2/2019 Radin
2019/0169299 A1 6/2019 Amin
2019/0183973 A1 6/2019 Hamilton
2019/0345253 A1 11/2019 Bansal
2019/0367622 A1 12/2019 Graham
2020/0246416 A1 8/2020 Radin
2020/0299393 A1 9/2020 Stahl
2020/0332014 A1 10/2020 Kostic
2020/0345843 A1 11/2020 Asrat
2021/0000949 A1 1/2021 Goulaouic et al.
2021/0038715 A1 2/2021 Hamilton
2021/0040222 A1 2/2021 Bansal
2021/0163611 A1 6/2021 Martin
2021/0220470 A1 7/2021 Bryce et al.
2021/0363237 A1 11/2021 Radin
2021/0363264 A1 11/2021 Hamilton
2022/0110999 A1 4/2022 Radin
2022/0220211 A1 7/2022 Orengo
2022/0298250 A1 9/2022 Bansal
2023/0159647 A1 5/2023 Stahl
2023/0293682 A1 9/2023 Hamilton
2024/0350625 A1 10/2024 Asrat

FOREIGN PATENT DOCUMENTS

EP 1113818 B1 5/2006
EP 2022507 A1 2/2009
EP 1527100 7/2009
JP 05-246874 9/1993
JP 2006-131623 5/2006
JP 2016521713 7/2016
RU 2162711 2/2001
RU 2283665 C2 9/2006
RU 2453303 C1 6/2012
RU 2552929 C1 6/2015
WO 1992/19259 11/1992
WO 1994/14975 7/1994
WO 2001/092340 12/2001
WO 2003/048083 6/2003
WO 2005/047331 5/2005
WO 2005/085284 9/2005
WO 2006/003407 1/2006
WO 2006/072564 7/2006
WO 2006/083390 8/2006
WO 2008/054606 5/2008
WO 2008/116149 9/2008
WO 2009/124954 10/2009
WO 2010/053751 5/2010
WO 2010/065557 6/2010
WO 2010/120524 10/2010
WO 2011/026966 3/2011
WO 2012/047954 4/2012
WO 2012/094643 7/2012
WO 2012/177945 12/2012
WO 2013/051928 4/2013
WO 2013/088109 6/2013
WO 2013/116287 8/2013
WO 2013/155010 10/2013
WO 2014/031610 2/2014
WO 2014/039461 3/2014
WO 2014/059178 4/2014
WO 2014/122144 8/2014
WO 2014/197470 12/2014
WO 2014/205365 12/2014
WO 2015/006571 1/2015
WO 2015/127229 8/2015
WO 2016/077675 5/2016
WO 2016/166629 10/2016
WO 2017/143270 8/2017
WO 2018/035393 2/2018
WO 2018/045130 3/2018
WO 2018/057776 3/2018
WO 2018/151836 8/2018
WO 2018/201051 11/2018
WO 2019/089473 5/2019
WO 2019/240288 12/2019
WO 2020/018820 1/2020
WO 2021/195530 9/2021

(56) References Cited

OTHER PUBLICATIONS

Yasuda, Naomi et al., "Comparison of serum-specific IgE measurement results between IMMULITE 2000 3gAllergy and ImmunoCAP", Technical Article, 2015, vol. 64, No. 6, pp. 727-736, with English summary.
Kegg: "Drug: D10354," Dupilumab, Sep. 2015, Accessible on the Internet Archive at URL: https://web.archive.org/web/20150929121012/http://genome.jp/dbget-bin/www_bget?dr:D10354, searched on Apr. 22, 2024, 1 page.
Screenshot of Website created by SSP. Co., Ltd (a pharmaceutical company located in Japan now a member of Sanofi global group), Jul. 4, 2016, located at URL: https://web.archive.org/web/20160704124211/https://www.ssp.co.jp/alesion/rhinitis, searched on Apr. 22, 2024, 6 pages with English translation.
Agosti, Jan et al., "Novel Therapeutic Approaches for Allergic Rhinitis", Immunology and Allergy Clinics of North America, May 2000, vol. 20, No. 2, pp. 401-423.
The American Academy of Allergy, Asthma, and Immunology, "The Current State or Oral Immunotherapy", retrieved from: https://www.aaaai.org/tools-for-the-public/conditions-library/allergies/the-current-state-or-oral-immunotherapy), Year: reviewed Feb. 4, 2020, 5 pages.
Sheldon, J. et al., "Allergy Diagnosis Reference Guide", Est Kent Hospitals University, Clinical Biochemistry, retrieved from: https://www.mtw.nhs.uk/wp/content/uploads/2015/08/Allergy_diagnosis_reference_guide.pdf, Oct. 2014, 10 pages.
Wang, J. et al., "0056 Baseline peanut-specific IgE potentially predicts up-dose completion and treatment response with AR10 in CODIT", Annals of Allergy, Asthma & Immunology, vol. 17, Issue 5, Supplemental, Nov. 2016, p. S18, 2 pages.
Parrish, Chris, "Management of Peanut Allergy: A Focus on Novel Immunotherapies", ALMC, 2018; vol. 24, Issue 19, SO, retrieved from: https://ajmc.com/view/management-of-peanut-allergy-a-focus-on-novel-immunotherapies, Oct. 19, 2018, 25 pages.
"AR101 Oral Immunotherapy for Peanut Allergy", N. Eng J Med 2018; 379; 1991-2001, located online on Jan. 24, 2023 at: https:///www.nejm.org/doi/full/10.1056/nejmoa1812856, 20 pages.
"Dupilumab therapy in moderate-to-severe atopic dermatitis provides positive results in the first two phase III clinical trials", J Int Pharm Res, vol. 43, No. 4, Aug. 31, 2016, p. 785 (with English translation).
Abe, Yasuhiko, et al., "Advances in the Diagnosis and Treatment of Eosinophilic Esophagitis", (English abstract), Gastroenterological Endoscopy, 2014, vol. 56, Issue 9, pp. 3378-3393.
Abonia et al. (Apr. 2013) Journal of Allergy Clin Immunol "High prevalence of eosinophilic esophagitis in patients with inherited connective tissue disorders", vol. 132, No. 2, pp. 378-386.
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.
Aceves et al. (Feb. 29, 2009) Immunol Allergy Clin N Am 29:197-211 "Relationships Between Eosinophilic Inflammation, Tissue Remodeling, and Fibrosis in Eosinophilic Esophagitis".
Akinlade, B. et al: "Conjunctivitis in dupilumab clinical trials", British Journal of Dermatology, (Mar. 9, 2019), pp. 1-15.
Akiyama, et al., A Study on Indoor Allergens Measured in Home Environments of Adult-Asthmatic Patients, Housing Research Foundation, Research Annual Report, 1997, No. 24, Study No. 9620, 1-10, English Synopsis Only.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (Aug. 10, 2011) Gastroenterology, vol. 141, No. 5, pp. 1593-1604, "An Antibody Against IL-5 Reduces Nos. of Esophageal Intraepithelial Eosinophils in Children with Eosinophilic Esophagitis".
Assa'ad, Amal, What is new in the Treatment of Eosinophilic Eosophagitis? Clinical and Translational Allergy 2011 (Suppl 1):S69, doi: 10.1186/2045-7022-1-S 1-S69.
Ayars, Andrew G. et al., "Pharmacologic Therapies in Pulmonology and Allergy", 2016 Med Clin N Am 100(4): 851-868.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balabolkin, I. et al., "Modern concepts of pathogenesis and therapy of atopic dermatitis in children", PHARMATEKA, 2017, No. 1, p. 53-60, with English translation, 14 pages.
Balint and Larrick (Dec. 27, 1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (Nov. 3, 2008) The Journal of Clinical Investigation 118(11):3546-3556 "The cytokine network in asthma and chronic obstructive pulmonary disease".
Barthelemy, Pierre et al., "Comprehensive analysis of the factors contributing to the stability and solubility of autonomous human VH domains", Journal of Biological Chemistry, 2008, 283:3639-3654.
Bateman et al. (2004) Am. J. Respir. Crit. Care Med. 170:836-844 "Can guideline-defined asthma control be achieved?", The Gaining Optimal Asthma Control Study.
Beck et al. (Jul. 10, 2014) New England Journal of Medicine 371(2): 130-139 "Dupilumab treatment in adults with moderate-to-severe atopic dermatitis".
Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.
Bergmann, M.M. et al., "Evaluation of Food Allergy in Patients with Atopic Dermatitis", J Allergy Clin Immunol, 1, pp. 22-28, Jan. 1, 2013.
Beyer et al. (Apr. 2, 2002) Journal of Allergy Clin Immunol 109(4):707-713 "Human milk-specific mucosal lymphocytes of the gastrointestinal tract display a $T_H2$ cytokine profile".
Bhardwaj and Ghaffari (Sep. 2012) Annals of Allergy, Asthma & Immunol 109 (3):155-159 "Biomarkers for eosinophilic esophagitis: a review".
Bieber, T., et al., "Atopic dermatitis: a candidate for disease-modifying strategy," Allergy 67 (2012) 969-975.
Blakely, Kim et al., "Dupilumab, a monoclonal antibody for atopic dermatitis: a review of current literature", Skin Therapy Letter, Mar.-Apr. 2016, vol. 21, No. 2, Dupilumab Clinical Trials in AD, 6 pages.
Blanchard and Rothenberg, (Feb. 2009) Immunol Allergy Clin N Am 29 (1):141-148 "Chemotactic Factors Associated with Eosinophilic Gastrointestinal Diseases".
Blanchard et al. (Jan. 1, 2011) J Allergy Clin Immunol 127(1):208-217 "A striking local esophageal cytokine expression profile in eosinophilic esophagitis".
Blanchard et al. (Dec. 2, 2007) Journal of Allergy Clin Immunol 120(6); 1292-1300, "IL-13 involvement in eosinophilic esophagitis: Transcriptome analysis and reversibility with glucocorticoids".
Blanchard et al. (Feb. 2006) The Journal of Clinical Investigation 116(2): 536-47, "Eotaxin-3 and a uniquely conserved gene-expression profile in eosinophilic esophagitis".
Blanchard et al. (Apr. 2010) The Journal of Immunology "Coordinate Interaction between IL-13 and Epithelial Differentiation Cluster Genes in Eosinophilic Esophagitis" vol. 184, No. 7, pp. 4033-4041.

(56) References Cited

OTHER PUBLICATIONS

Blanchard et al. (Aug. 24, 2005) Clin Exp Allergy 35 (8):1096-1103 "Inhibition of human interleukin-13-induced respiratory and oesophageal inflammation by anti-human-interleukin-13 antibody (CAT-354)".
Blankestijn, Mark et al., "Could Duratumumab be used to treat severe allergy?", Journal of Allergy and Clinical Immunology, vol. 139, No. 5, Jan. 19, 2017, p. 1677-1678.e3.
Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17)31191-1, 65 pgs.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
BSACI News Report confirming BSACI conference date of Jul. 8-10, 2013, 2 pages.
Burmeister-Getz et al. (2009) J. Clin. Pharmacol. 49:1025-1036, "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology 6(4); 740-50, Nov. 14, 2012, doi:10.1038/mi.2012.112.
Busse, et al., "Efficacy of dupilumab on clinical outcomes in patients with asthma and perennial allergic rhinitis", Ann Allergy Asthma Immunol 125 (2020); 565-576.
Caldas et al. (2003) Molecular Immunology 39:941-952 "Humanization of the anti-CD18 antibody 6.7: an unexpected effect of a framework residue in binding to antigen".
Caraccio, Chiara et al., "Bispecific Antibodies for Multiple Myeloma: A Review of Targets, Drugs, Clinical Trials, and Future Directions", Frontiers in Immunology, Apr. 2020, vol. 11, Article 501, pp. 1-25.
Carr, Warner, "Topical Calcineurin Inhibitors for Atopic Dermatitis: Review and Treatment Recommendations", Pediatric Drugs, 2013, vol. 15, pp. 303-310.
Carter, Paul J., (May 2006) The Journal of Immunology 6:(5);343-357 "Potent Antibody Therapeutics by Design".
Casset et al. (2003) Biochemical and Biophysical Research Communication 307:198-205 "A peptide mimetic of an anti-CD4 monoclonal antibody by rational design".
Celakovska, J. et al., "Sensitization to aeroallergens in atopic dermatitis patients: association with concomitant allergic diseases", JEADV 2015; 29, 1500-1505.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Chan, L.S. et al., "Expression of Interleukin-4 in the epidermis of transgenic mice results in pruritic inflammatory skin disease: an experimental animal model to study atopic dermatitis", J. Invest. Dermatol., Oct. 1, 2001, 117(4): 977-983.
Chehade and Sampson (Feb. 2009) Immunol Allergy Clin N Am 29:149-158 "The Role of Lymphocytes in Eosinophilic Gastrointestinal Disorders".
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Choi, Yoonjoo et al., "Predicting antibody complementarity determining region structures without classification", Molecular Biosystems, 2011, 7:3327-334.
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.
Clinical Trials, Study NCT00436670, "Phase II Study to Evaluate the Efficacy of AMG 317", first posted Feb. 19, 2007, Amgen actual study completion date—Feb. 2009, 7 pages.
Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Clinical Trials, Study NCT01859988, phase 2b, "Study of Dupilumab Administered to Adult Patients With Moderate-to-Severe Atopic Dermatitis", study completion date—Sep. 2014, 10 pages.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov Identifier: NCT02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.
Corren et al., "A Randomized, Controlled, Phase 2 Study of AMG 317, an IL-4R Antagonist, in Patients with Asthma", (2010) American Journal of Respiratory and Critical Care Medicine 181(8):788-796.
Corren, J. et al., "Effects of combined treatment with allergen immunotherapy and dupilumab on nasal allergen challenge and tolerability in immunotherapy", Allergy, Jun. 6, 2020, p. 78.

(56) References Cited

OTHER PUBLICATIONS

Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
Cortes, J.R., et al., Proton pump inhibitors inhibit IL-4 and IL-13 signaling stat6 activation, European Journal of Immunology, (Sep. 2009) vol. 39, pp. 5204, Supp.
D'Erme, Angelo et al., "Spotlight on dupilumab in the treatment of atopic dermatitis: design, development, and potential place in therapy", Drug Des Devel Ther, 2017, vol. 11, p. 1473-1480, DOI: 10.2147/DDDT.S113192, Abstract, c.1475-1478, 8 pages.
Database Embase [Online], Elsevier Science Publishers, Amsterdam, NL; (May 1, 2019), Cork M. J: "605 Efficacy and safety of dupilumab in adolescent patients with moderate-to-severe atopic dermatitis", XP002793331, Database accession No. EMB-002001809007 abstract.
Database Embase [Online], Elsevier Science Publishers, Amsterdam, NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract.
Davies et al. (1996) Immunotechnol. 2(3):169-179 "Affinity improvement of single antibody VH domains: residues in all three hypervariable regions affect antigen binding".
Davis (Aug. 2004) Seminars in Immunology 16(4):239-243 "The evolutionary and structural 'logic' of antigen receptor diversity".
De Genst, Erwin et al., "Antibody repertoire development in camelids", Developmental and Comparative Immunology, 30 (2006); 187-198.
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14-19, 2016, retrieved from the Internet on Sep. 20, 2018 at: https://www.eventscribe.com/2016/ACG/QRcode.asp?Pres=178380, 3 pages.
Dellon, Evan Se., (Apr. 27, 2013) Dig Dis Sci, vol. 58, pp. 1445-1448, "The Pathogenesis of Eosinophilic Esophagitis: Beyond the Eosinophil".
Desreumaux et al. (Mar. 1, 1996) Gastroenterology 110(3):768-774 "Interleukin 3, Granulocyte-Macrophage Colony-Stimulating Factor, and Interleukin 5 in Eosinophilic Gastroenteritis".
Dupixent (dupilumab) Injection, for Subcutaneous Use, Patient Information, Issued Mar. 2017, 34 pages.
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, mailed Feb. 22, 2019, 34 pages.
Fillon et al. (2009) Immunol Allergy Clin N Am 29(1):171-178 "Epithelial Function in Eosinophilic Gastrointestinal Diseases".
Finkelman, Fred, et al., "Regulation of murine in vivo IgG and IgE responses by a monoclonal anti-IL-4 receptor antibody", Jun. 1991;3(6); 599-607.
Foote and Winter (1992) J. Mol. Biol. 224:487-499 "Antibody Framework Residues Affecting the Conformation of the Hypervariable Loops".
Foroughi et al. (Sep. 1, 2007) J Allergy Clin Immunol 120(3):594-601 "Anti-IgE Treatment of Eosinophil Associated Gastrointestinal Disorders".
Franciosi and Liacouras, (Feb. 2009) Immunol Allergy Clin N Am 29(1):19-27, "Eosinophilic Esophagitis".
Garraud, Olivier, et al., "Regulation of immunoglobulin production in hyper-IgE (Job's) syndrome", J. Allergy Clin. Immunol., Feb. 1999. (2 Pt. 1): 333-340.
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gaugris, Sabine et al., "Burden of Concomitant Allergic Rhinitis in Adults with Asthma", Journal of Asthma 43:1-7 (2006).
Gavett et al. (1997) The American Physiological Society, 16(2):L253-L261, "Interleukin-4 receptor blockade prevents airway responses induced by antigen challenge in mice".
Gevaert et al. (2006) Journal of Allergy and Clinical Immunology 118(5):1133-1141, "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Grechkina, L.I. et al., "Characteristics for the physical development indices demonstrated by adolescents boring in Magadan", Siberian Medical Journal, 2013, No. 3, Results and discussion, Table 1, obtained from: https://cyberleninka.ru/article/n/harakteristika-pokazateley-fizicheskogo-razvitiya-podrostkov-urozhentsev-magadana/viewer, with English translation, 9 pages.
Griffiths, Andrew et al., "Human anti-self antibodies with high specificity from phage display libraries", The EMBO Journal, 1993, 12:725-734.
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Guidelines for the Prevention and Treatment of Allergic Diseases, Xixin Yan and Jitao Guan as editors-in-chief, Shijiazhuang: Hebei Science and Technology Press, relevant pp. 252-254, published in May 2009, numbered pp. 1-4 (20 pages total).
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Hamilton, Jennifer et al., "Dupilumab Normalizes the Eosinophilic Esophagitis Disease Transcriptome In Adult Patients With Eosinophilic", May 1, 2020, Abstract, retrieved from internet on Aug. 5, 2021 at: https://www.sciencedirect.com/science/atricle/pii/S0016508520327669?via%3Dihub, 1 page.
Harris, Jeffrey et al., "A randomized trial of the efficacy and safety of quilizumab in adults with inadequately controlled allergic asthma", Respiratory Research (2016) 17:29, 11 pages.
Highlights of Prescribing Information, DUPIXENT (dupilumab) injection, for subcutaneous use Initial U.S. Approval: 2017, U.S. Food and Drug Administration (FDA), Revised Mar. 2017.
Hijnen et al. (Feb. 2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hill, Robert et al., "Comparison of drug delivery with autoinjector versus manual prefilled syringe and between three different autoinjector devices administered in pig thigh", Med Devices (Auckl), 2016, 9; 257-266, pub. Online Aug. 2, 2016, doi: 10.2147/MDER.S83406.
Hirano, Ikuo et al., "Dupilumab Efficacy and Safety in Adult Patients with Active Eosinophilic Esophagitis: a Randomized Double-

(56) References Cited

OTHER PUBLICATIONS

Blind Placebo-Controlled Phase 2 Trial", The World of Congress Gastroenterology ACG, Orlando, FL, Oct. 13-18, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113 Abstract—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490, "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?".
Huang, Evie et al: "Severe Atopic Dermatitis in Children", Current Allergy and Asthma Reports, Current Science, US, vol. 18, No. 6, May 10, 2018, pp. 1-8.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
International Investigative Dermatology, Edinburgh, Conference Posters, May 8-11, 2013, 4 pages.
Ivashkin, V. T., et al., "Eosinophilic esophagitis," a textbook for physicians, Moscow, "AISPI RAS" JSC, Feb. 14, 2013, pp. 13-21, 57-62, with complete English translation, 50 pages all together.
Ivashkin, V. T., et al., "Eosinophilic esophagitis: literature review and description of own survey," RJGHC, 2012, vol. 22, 1, pp. 71-81.
Jahnz-Rozyk et al. (Apr. 6, 2005) Allergy 60(5):685-688, "Serum thymus and activation-regulated chemokine, macrophage-derived chemokine and eotaxin as marker of severity of atopic dermatitis".
Janeway, Jr. et al., Immunobiology, 3rd Edition, 1997, Garland Publishing Inc., pp. 11:1-11:22.
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608, "Tuning sensitivity to IL-4 and IL-13: differential expression of IL-4Rα, IL-13Rα1, and γc regulates relative cytokine sensitivity".
Jyonouchi et al. (2013) Basic Mechanisms in Allergic Disease, Clinical & Experimental Allergy, vol. 44, No. 1. pp. 58-68, "Invariant Natural Killer T cells in children with Eosinophilic Esophagitis".
Kagami et al. (2003) Clin. Exp. Immunology 134(2):309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al., (2002) Clin. Exp. Immunol 127(2):270-273 "Serum macrophage-derived chemokine (MDC) levels are closely related with the disease activity of atopic dermatitis".
Kakinuma, Takashi et al., (Mar. 1, 2001) J. Allergy Clin. Immunol. 107(3):535-541, "Thymus and activation-regulated chemokine in atopic dermatitis: Serum thymus and activation-regulated chemokine level is closely related with disease activity".
Kakkar, Tarundeep et al., (2011) Pharmaceutical Research 28(10):2530-2542, "Population PK and IgE Pharmacodynamic Analysis of a Fully Human Monoclonal Antibody Against IL4 Receptor".
Katial, Rohit, (Feb. 2009) Immunol Allergy Clin N Am 29(1):119-127 "Biomarkers for Nononcologic Gastrointestinal Disease".
Kelly, Ludmila and Liu, Xia (2014) World Allergy Organization Journal 7(S1):P8 "Poster 1013: IL-4R alpha antibody inhibits IgE production and airway remodeling in mouse model of house dust mite-induced eosinophilic asthma", 1 page.
Kharkevich, D.A., Pharmacology (Farmakologiya: A Scholarly Manual), 10th Ed., Moscow: GEOTAR-Media, 2010, pp. 73-74 and pp. 846-847, with English translation of cited pages, 12 pages total.
Kim et al., "Engineering of anti-human interleukin-4 receptor alpha antibodies with potent antagonistic activity", Scientific Reports, 2019, vol. 9, Article No. 7772, pp. 1-12.
Kim et al., (Dec. 1, 2004) J Allergy Clin Immunol 114(6):1449-1455, "Rebound eosinophilia after treatment of hypereosinophilic syndrome and eosinophilic gastroenteritis with monoclonal anti-IL-5 antibody SCH55700".
Klimka et al., "Human anti-CD30 recombinant antibodies by guided phage antibody selection using cell planning", British Journal of Cancer, 2000, 83:252-260.
Konikoff et al., (Nov. 1, 2006) Gastroenterology 131(5):1381-1391, "A Randomized, Double-Blind, Placebo-Controlled Trial of Fluticasone Propionate for Pediatric Eosinophilic Esophagitis".
Kopf et al. (1993) Letters to Nature 362:245-248, "Disruption of the murine IL-4 gene blocks Th2 cytokine responses".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Kostic et al. (2010) Clinical Immunology 135:S105-S106, "A Fully Human IL4Rα Antibody for Inhibition of IL-4/IL-13-driven TH2 Responses in Allergic Disease".
Kottyan et al. (Aug. 2014) Nature Genetics, vol. 46, No. 8, pp. 895-900, "Genome-wide association analysis of eosinophilic esophagitis provides insight into the tissue specificity of this allergic disease".
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Kulis et al. (2011) J. Allergy Clin Immunol 127(1):81-88 "Single-tree nut immunotherapy attenuates allergic reactions in mice with hypersensitivity to multiple tree nuts".
Kussie, Paul, et al., "A Single Engineered Amino Acid Substitution Changes Antibody Fine Specificity", Journal of Immunology:152, pp. 146-152, 1994.
Kwiatek, Monika et al., "Mechanical properties of the esophagus in eosinophilic esophagitis" Gastroenterology, 2011, vol. 140, No. 1, pp. 82-90.
Leung et al. (Apr. 2004) The Journal of Clinical Investigation 113(5): 651-657 "New insights into atopic dermatitis".
Leung et al., (Mar. 13, 2003) The New England Journal of Medicine 348(11):986-993 "Effect of Anti-IgE Therapy in Patients with Peanut Allergy".
Lezcano-Meza et al., (2003) Allergy 58(10):1011-1017, "Interleukin (IL)-4 and to a lesser extent either IL-13 or interferon-gamma regulate the production of eotaxin-2/CCL24 in nasal polyps".
Liacouras et al., (Apr. 8, 2011) J Allergy Clin Immunol 128(1):3-20, "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".
Linden, Carey et al., "Analysis of allergen specific IgE cut points to cat and dog in the Childhood Allergy Study", Annals of Allergy, Asthma & Immunology, 2011, 106.2: 153-158. e2.
Liu et al., (Aug. 9, 1999) Gene Therapy 6(7):1258-1266 "Hydrodynamics-based transfection in animals by systemic administration of plasmid DNA".
Lucae, S. et al., "IgE responses to exogenous and endogenous allergens in atopic dermatitis patients under long-term systemic cyclosporine A treatment", Allergy 71 (2016); 115-118.

(56) References Cited

OTHER PUBLICATIONS

Lucendo and Sanchez-Cazalilla, (Nov. 1, 2012) Expert Rev. Clin. Immunol. 8(8):733-745 "Adult versus pediatric eosinophilic esophagitis: important differences and similarities for the clinician to understand".
Lwin et al., (Apr. 2011) Modern Pathology 2(4)4:556-563, "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al., (1994) Proc. Soc. Exp. Biol. Med. 206(3):233-237 "In vivo biological effects of recombinant soluble interleukin-4 receptor".
Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.
Mannon et al., (2012) Gut 61(12):1765-1773, "Interleukin 13 and its role in gut defence and inflammation".
Mariuzza et al. (1987) Ann. Rev. Biophys. Biophys. Chem. 16:139-159 "The Structural Basis of Antigen-Antibody Recognition".
Marone et al., Dec. 6, 2019, "The Intriguing Role of Interleukin 13 in the Pathophysiology of Asthma", Frontiers in Pharmacology, vol. 10, pp. 1-13.
Martel, Britta C., et al., "Translational animal Models of Atopic Dermatitis for Preclinical Studies," Yale Journal of Biology and Medicine 90 (2017), pp. 389-402.
Mashkovsky, M.D., Medicinal Drugs: Manual for Physicians, vol. 1, 14th Ed., v1:8-9, Moscow, 2001 Medicines, 7 pgs. (with English translation).
Masterson et al., (Oct. 2011) Curr Opin Gastroenterol. 27(6):515-522, "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg, (Nov. 1, 2003) Gastroenterology 125(5):1419-1427 "Intratracheal IL-13 Induces Eosinophilic Esophagitis by an IL-5, Eotaxin-1, and STAT6-Dependent Mechanism".
Mishra et al., (Jan. 1, 2001) J Clin. Invest. 107(1):83-90 "An etiological role for aeroallergens and eosinophils in experimental esophagitis".
Mishra et al., (Mar. 1, 2002) The Journal of Immunology 168(5):2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al., (Sep. 23, 2011) Clinical & Experimental Allergy 42(5):712-737, "Molecular and clinical rationale for therapeutic targeting of interleukin-5 and its receptor".
Morioka et al., (2009) British Journal of Dermatology 160(6):1172-1179, "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta 1592, (2002), 237-250.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Müller et al. (1993) Journal of Immunology 150:5576-5584 "Th2 cells mediate IL-4-dependent local tissue inflammation".
Nadeau et al., (Jun. 2011) J. Allergy Clin. Immunol 127(6): 1622-1624, Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
NCT03682770, USNLM (U.S. National Library of Medicine), History of Changes for Study, NCT03682770: Study in Pediatric Subjects With Peanut Allergy to Evaluate Efficacy and Safety of Dupilumab as Adjunct to AR101 (Peanut Oral Immunotherapy), https:clinicaltrials.gov/ct2/history/NCT03682770?V_4=View, 2019, 7 pages.
Nguyen et al. (Jul. 2011) Immunological Reviews 242(1):258-271 "Immune modulation for treatment of allergic disease".
Nguyen, Tran Hoai et al., "FutureForms of Immunotherapy and Immunomodulators in Allergic Disease", Immunol Allergy Clin N Am 31 (2011); 343-365.
Nicodeme et al., "Esophageal Distensibility as a Measure of Disease Severity in Patients with Eosinophilic Esophagitis", Clinical Gastroenterology and Hepatology, Sep. 2013, vol. 11, No. 9, pp. 1101-1107.
Niederberger, Verena, (Feb. 2009) Immunology Letters 122, Issue 2:131-133 "Allergen-specific immunotherapy".
Niranjan et al., (2013) Immunology and Cell Biology pp. 1-8, "Pathogenesis of allergen-induced eosinophilic esophagitis is independent of interleukin (IL)-13".
Noel et al. (Aug. 26, 2004) The New England Journal of Medicine 351:940-941 "Eosinophilic Esophagitis".
Nomura, Ichiro et al., "*Staphylococcus aureus* and Atopic Dermatitis", (2000), IRYO vol. 54, No. 2, pp. 62-66, 18 pages with English translation.
Novartis Pharmaceuticals (2013) QAX576, "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell, 171, 217-228.
Oh et al., (2010) Eur Respir Rev 19(115):46-54 "Investigational therapeutics targeting the IL-4/IL-13/STAT-6 pathway for the treatment of asthma".
Ohno et al., (May 1, 1985) Proc. Natl. Acad. Sci. USA 82(9):2945-2949, "Antigen-binding specificities of antibodies are primarily determined by seven residues of $V_H$".
Ong Peck, (2012) Expert Opinion on Emerging Drugs 17(2):129-133 "Editorial update on emerging treatments of atopic dermatitis".
Otani et al., (2013) Journal of Allergy and Clinical Immunology 131(6):1576-1582, "Anti-IL-5 therapy reduces mast cell and IL-9 cell numbers in pediatric patients with eosinophilic esophagitis".
Otulana et al., (2011) Am. J. Respir. Crit. Care Med. 183:A6179, "A Phase 2b Study of Inhaled Pitrakinra, An IL-4R/IL-13 Antagonist, Successfully Identified Responder Subpopulations of Patients with Uncontrolled Asthma".
Oyoshi et al., (Jan. 1, 2009) Advances in Immunology 102:135-226, "Cellular and Molecular Mechanisms in Atopic Dermatitis".
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Pesek, Robert D. et al., "Emerging drugs for eosinophilic esophagitis", Expert Opinion on Emerging Drugs, vol. 23, No. 2, Apr. 3, 2018, 12 pages.
Peserico et al., (2008) British Journal of Dermatology 158(4):801-807, "Reduction of relapses of atopic dermatitis with methylprednisolone aceponate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Phan, N.Q et al., "Assessment of pruritis intensity: prospective study on validity and reliability of the visual analogue scale, numeric rating scale, and verbal rating scale in 471 patients with chronic pruritis", Acta Dermato-Venereologica, 2012, vol. 92: 502-507.

(56) References Cited

OTHER PUBLICATIONS

Prieto and Richter, (May 24, 2013) Curr Gastroenterol Rep 15(6):324, "Eosinophilic Esophagitis in Adults: an Update on Medical Management".
Prussin et al., (Dec. 1, 2009) J Allergy Clin Immunol. 124(6):1326-1332, "Eosinophilic gastrointestinal disease and peanut allergy are alternatively associated with IL-5+ and IL-5-TH2 responses".
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., p. AB158, (made available on Jan. 26, 2013), 2 pgs.
Rafi et al., (Jan. 1, 2010) Allergy and Asthma Proceedings 31(1):76-83 "Effects of omalizumab in patients with food allergy".
Rayapudi et al., Aug. 2010, Journal of Leukocyte Biology 88(2): 337-346, "Indoor insect allergens are potent inducers of experimental eosinophilic esophagitis in mice".
Receptos, Inc. Annual Report Pursuant to Section 13 or 15(D) of the Securities Exchange Act of 1934, filed Mar. 6, 2014 for fiscal period ending Dec. 31, 2013, Edgar Online, 177 pages.
Reed, Craig, et al., "Patient-reported outcomes in esophageal diseases", Clinical Gastroenterology and Hepatology, Elsevier, Amsterdam, NL, vol. 16. No. 3, pp. 305-310.
Regeneron 2011 Annual Report (Apr. 2011), 12 pages.
Regeneron Pharmaceuticals et al., "Dupilumab As An Adjunct for Subcutaneous Grass Immunotherapy", May 11, 2020, retrieved from Internet at: https://clinicaltrials.gov/ct2/history/NCT03558997?V_5=View#StudyPageTop, retrieved on Oct. 20, 2020, 46 pgs.
Regeneron Pharmaceuticals et al., "Dupilumab As An Adjunct for Subcutaneous Grass Immunotherapy", Jun. 26, 2019, retrieved from Internet at: https://clinicaltrials.gov/ct2/history/NCT03558997?A=4&B=4&C=merged#StudyPageTop, retrieved on Oct. 20, 2020, 10 pgs.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent _FPI.pdf, 4 pages.
Ring et al., (2012) J. Eur. Acad. Dermatol. Venereol. 26(8):1045-1060, "Guidelines for treatment of atopic eczema (atopic dermatitis) Part 1".
Roitt et al., (2001) Mosby-Harcourt Publishers Limited, Immunology- Sixth Edition "Antigen Presentation" pp. 110-111.
Roll et al., (Jan. 1, 2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, Special Issue, pp. 44-47. (with English translation of the cited portion).
Rothenberg, (2004) J Allergy Clin Immunol 113(1):11-28, "Eosinophilic gastrointestinal disorders (EGID)".
Rothenberg, (2009) Gastroenterology 137(4):1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2014, pp. 500-507.
Rudikoff et al. (1982) Proc. Natl. Acad. Sci. 79:1979-1983 "Single amino acid substitution altering antigen-binding specificity".
Russian Office Action and Search Report in Application 2020140639, mailed Aug. 17, 2022, with English translation, 26 pages.
Russian Official Action from Russian Federation for RU Application 2016104400, mailed Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), with English translation of the Abstract only, cited in the Japanese Patent Application No. 2015-531149.
Sampson et al., (May 2011) J. Allergy Clin Immunol. 127(5): 1309-1310, Letters to the Editor, "A phase II, randomized, double-blind, parallel-group, placebo-controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al., (1993) J. Immunol. 150(7):2717-2723, "Recombinant soluble murine IL-4 receptor can inhibit or enhance IgE responses in vivo".
Scavuzzo et al., (2005) Biomedicine & Pharmacotherapy 59(6):323-329, "Inflammatory mediators and eosinophilia in atopic and non-atopic patients with nasal polyposis".
Schmid, J.M. et al., "Basophil Sensitivity Decreases During the Updosing on SCIT in Subjects Allergic to Grass Pollen", Journal of Allergy and Clinical Immunology, vol. 127, No. S2, Feb. 1, 2011, p. AB203.
Schmidt-Weber, (Mar. 13, 2012) Chem Immunol Allergy 96:120-125, "Anti-IL-4 as a New Strategy in Allergy".
Schmitt et al., (Dec. 1, 2007) J. of Allergy and Clinical Immunology 120(6):1389-1398, "What are the best outcome measurements for atopic eczema? A systematic review".
Schneider et al., (Sep. 26, 2013) J. Allergy Clin Immunol 132(6):1368-1374, "A pilot study of omalizumab to facilitate rapid oral desensitization in high-risk peanut-allergic patients".
Sekiya et al., (2002) Allergy 57(2):173-177, "Increased levels of a TH2-type CC chemokine thymus and activation-regulated chemokine (TARC) in serum and induced sputum of asthmatics".
Siegfried et al., "Use of dupilumab in pediatric atopic dermatitis: Access, dosing, and implications for managing severe atopic dermatitis", Pediatric Dermatology, vol. 36, No. 1, Jan. 2019, pp. 172-176.
Silverberg et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA, 1 page.
Silverberg et al., P481, "Dupilumab treatment rapidly improves itch in patients with moderate-to-severe atopic dermatitis" An Allergy Asthma Immunol. 2017;119(suppl 5):S95.
Simpson, E.L., et al., "Two Phase 3 Trials of Dupilumab versus Placebo in Atopic Dermatitis," The New England Journal of Medicine, Oct. 1, 2016, 14 pages, DOI: 10.1056/NEJMoa1610020.
Simpson, Eric L. et al., (Jan. 14, 2016), J. Am. Acad. Dermatol. 74(3):491-498, "Patient burden of moderate to severe atopic dermatitis (AD): Insights from a phase 2b clinical trial of dupilumab in adults".
Simpson, Eric L. et al., (Jun. 4, 2016), J. Am. Acad. Dermatol. 75(3):506-515, "Dupilumab therapy provides clinically meaningful improvement in patient-reported outcomes (PROs): A phase IIb, randomized, placebo-controlled, clinical trial in adult patients with moderate to severe atopic dermatitis (AD)".

(56) References Cited

OTHER PUBLICATIONS

Slager et al. (Apr. 26, 2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al., (Dec. 1, 2006) J Allergy Clin Immunol 118(6):1312-1319, "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al., (Dec. 2008) Clinical & Experimental Allergy 38(12):1858-1865, "Immunomodulatory therapy of eosinophil-associated gastrointestinal diseases".
Strauman, (2009) Immunol Allergy Clin N Am 29(1):11-18, "Clinical Evaluation of the Adult who has Eosinophilic Esophagitis".
Straumann et al., (2001) J Allergy Clin Immunol 108(6): 954-961 "Idiopathic eosinophilic esophagitis is associated with a $T_H2$-type allergic inflammatory response".
Straumann et al., (2009) Gut vol. 59(1):21-30, "Anti-interleukin-5 antibody treatment (mepolizumab) in active eosinophilic oesophagitis: a randomized, placebo-controlled, double-blind trial".
Straumann, (2005) J Allergy Clin Immunol 115(2):418-419, "Eosinophilic esophagitis: Escalating epidemiology?".
Supplementary Appendix, Supplement to: AR101 Oral Immunotherapy for Peanut Allergy, N Engl J Med 2018, 379; 1991-2001, DOI: 10.1056/NEJMoa1812856, 2018, last updated Mar. 7, 2019, 23 pages.
Takashi Yoshike, "Treatment for Atopic Dermatitis", Juntendo Medical Journal, 1999, vol. 45, No. 3, pp. 352-360, 33 pages with English translation.
Tazawa et al., (2004) Arch Dermatol Res 295:459-464, "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Terui, et al., (2000) "Learning from Fungus Allergy in Atopic Dermatitis Patients," Japan J. Med. Mycol, vol. 41, No. 3, 157-160.
Thaci, Diamant et al., Oct. 8, 2015), "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, 387(10013):40-52.
Tomkinson et al., (2001) J. Immunol 166(9):5792-5800, "A Murine IL-4 Receptor Antagonist that Inhibits IL-4- and IL-13-induced Responses Prevents Antigen-Induced Airway Eosinophilia and Airway Hyperresponsiveness".
Tsianakas, Athanasios et al., "Dupilumab: A Milestone in the Treatment of Atopic Dermatitis," The Lancet, (Oct. 8, 2015), 387(10013):4-5.
Ul-Haq, Zaheer et al., "Interleukin-4 receptor signaling and its binding mechanism: A therapeutic insight from inhibitors tool box", Cytokine & Growth Factor Review (2016), 32:3-15.
Vajdos et al. (2002) Journal of Molecular Biology 320(2):415-428 "Comprehensive functional maps of the antigen-binding site of an anti-ErbB2 antibody obtained with shotgun scanning mutagenesis".
Vakharia, Paras P. et al., (2017), "Monoclonal Antibodies for Atopic Dermatitis: Progress and Potential", BioDrugs 31:409-422.
Valovirta, Erkka et al., "Survey on the impact of comorbid allergic rhinitis in patients with asthma", BMC Pulmonary Medicine, Nov. 30, 2006, 10 pages.
Veerappan et al., (2009) Clinical Gastroenterology and Hepatology 7(4):420-426, "Prevalence of Eosinophilic Esophagitis in an Adult Population Undergoing Upper Endoscopy: A Prospective Study".
Vestergaard et al., (2000) The Journal of Investigative Dermatology 115(4):640-646, "A $Th_2$ Chemokine, TARC, Produced by Keratinocytes May Recruit $CLA^+CCR4^+$ Lymphocytes into Lesional Atopic Dermatitis Skin".
Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.
Virchow et al., (1994) Lung 172(6):313-334, "Cellular and immunological markers of allergic and intrinsic bronchial asthma".
Waccholz et al., "Detection of Allergen-Specific IgE Antibody Responses", 2005, Journal of Immunotoxicology, 1:3-4, 189-199.
Walker et al., (1993) Clinical and Experimental Allergy 23:145-153, "Atopic dermatitis: correlation of peripheral blood T cell activation, eosinophilia and serum factors with clinical severity".
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Wang and Liu, (2008) Current Opinion in Immunology 20:697-702 "The IL-17 cytokine family and their role in allergic inflammation".
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Ward, E. Sally et al., "Blinding activities of a repertoire of single immunoglobin variable domains secreted from *Escherichia coli*", Nature, 1989, 341:544-546.
Wark et al., (Aug. 7, 2006) Advanced Drug Delivery Reviews 58(5-6):657-670, "Latest technologies for the enhancement of antibody affinity".
Watson et al. (2011) Allergy, Asthma & Clinical Immunology 7:S4 "Atopic dermatitis".
Weber, et al. (Mar. 13, 2012) "Anti-IL-4 as a New Strategy in Allergy", Chemical immunology and Allergy, vol. 96, pp. 120-125.
Wegmann et al., "Targeting Cytokines in Asthma therapy: could IL-37 be a Solution?", Expert Review of Respiratory Medicine, 2017, vol. 11, No. 9, pp. 675-677.
Weihrauch et al., (2005) Cancer Research 65(13):5516-5519 "Elevated Serum Levels of CC Thymus and Activation-Related Chemokine (TARC) in Primary Hodgkin's Disease: Potential for a Prognostic Factor".
Weinbrand-Goichberg et al., (2013) Immunol Res 56(2): 249-260, "Eosinophilic esophagitis: an immune-mediated esophageal disease".
Wenzel et al. (2010) European Respiratory Society, Annual Congress 2010, "ERS—Programme" pp. 3980.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Wenzel et al., (2007) Lancet 370(9596):1422-1431, "Effect of an interleukin-4 variant on late phase asthmatic response to allergen challenge in asthmatic patients: results of two phase 2a studies".
Wenzel et al., May 21, 2013, New England Journal of Medicine 368(26):2455-2466, "Dupilumab in Persistent Asthma with Elevated Eosinophil Levels".
Wershil, Barry, (Feb. 1, 2009) Immunol Allergy Clin N Am 29(1):189-195, "Exploring the Role of Mast Cells in Eosinophilic Esophagitis".
Whalley et al., (Feb. 2004) British Journal of Dermatology 150:274-283, "A new instrument for assessing quality of life in atopic dermatitis: international development of the Quality of Life Index for Atopic Dermatitis (QoLIAD)".
Wilhelm and Stockinger, (Nov. 28, 2011) Frontiers in Immunology 2(68):1-4, "Innate lymphoid cells and type 2 (Th2) mediated immune responses-pathogenic or beneficial?".
Wills-Karp and Finkelman, (2008) Science Signaling 1(51):1-5, "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".

(56) References Cited

OTHER PUBLICATIONS

Winter and Harris (1993) Immunology Today 14(6):243-246 "Humanized Antibodies".
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Wong, et al., "Guidelines for the management of atopic dermatitis (eczema) for pharmacists," CPJ/RPC, Sep./Oct. 2017, vol. 150, No. 5, pp. 285-297.
Wu et al. (1999) Journal of Molecular Biology 294:151-162 "Humanization of a murine monoclonal antibody by simultaneous optimization of framework and CDR residues".
Yamanaka et al., (2011) Curr Probl Dermatol 41:80-92, "The Role of Cytokines/Chemokines in the Pathogenesis of Atopic Dermatitis".
Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Yan and Shaffer (2006) World J Gastroenterol 12(15):2328-2334 "Eosinophilic esophagitis: A newly established cause of dysphagia".
Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Zuo et al., (2010) Journal of Immunology 185:660-669, "IL-13 Induced Esophageal Remodeling and Gene Expression by an Eosinophil-Independent, IL-13R{alpha}2-Inhibited Pathway".
Zurawski et al., (1995) J. Biol. Chem. Am. Society of Biolochemical Biologists 270(23):13869-13878, "The primary binding subunit of the human Interleukin-4 receptor is also a component of the Interleukin-13 receptor".
Rial, Manual Jorge et al., "Dupilumab for Treatment of Food Allergy", J Allergy Clin Immunol Pract, Feb. 1, 2019, pp. 673-674.
Fujieda, Shigeharu et al., "Biomarkers in Allergic Rhinitis", Allergy, 2013, vol. 62, No. 5, pp. 523-531, with English translation (12 pages).
Nelson, M.R. et al., "Standardized Grass Allergen Extract Prescribing Practices in a Large Healthcare System", Journal of Allergy and Clinical Immunology, Abstract 486, Feb. 2008, vol. 121, Issue 2, Supplement 1, p. S126.
Nicholson, G. C. et al., "The effects of an anti-IL-13 mAB on cytokine levels and nasal symptoms following nasal allergen challenge", 2011, J. Allergy Clin Immunol., 128(4), pp. 800-807, 17 pgs all together.
European Communication of a Notice of Opposition in Application 17771619.8, mailed May 6, 2025, 43 pages.
European Communication of a Notice of Opposition in Application 17771619.8, mailed May 6, 2025, 37 pages.
European Communication of a Notice of Opposition in Application 17771619.8, mailed May 6, 2025, 28 pages.
European Communication of a Notice of Opposition in Application 17771619.8, mailed May 6, 2025, 35 pages.
European Opposition in 17771619.8, "Consolidated List" of cited art references, 4 pages.
Press release of Clinic Barcelona dated Mar. 2, 2016, "Immunotherapy proves to be effective for the treatment of chronic rhinosinusitis with nasal polyps", https://www.clinicbarcelona.org/en/news/immunotherapy-proves-to-be-effectivefor-the-treatment-of-chronic-rhinosinusitis-with-nasal-polyps. (also referred to as "Clinic Barcelona press release").
Salo P.M. et al. "Allergy-related outcomes in relation to serum IgE: results from the National Health and Nutrition Examination Survey 2005-2006", J Allergy Clin Immunol. May 2011;127(5):1226-35. e7. doi: 10.1016/j.jaci.2010.12.1106. Epub Feb. 12, 2011. PMID: 21320720; PMCID: PMC3108140. (also referred to as "Salo, 2011").
Chervinsky P. et al. "Omalizumab, an anti-IgE antibody, in the treatment of adults and adolescents with perennial allergic rhinitis", Ann Allergy Asthma Immunol. Aug. 2003;91(2):160-7. d□i: 10.1016/Sl081-1206(10)62171-0. PMID: 12952110. (also referred to as "Chervinsky, 2003").
Nayak A. and Langdon R.B. "Montelukast in the treatment of allergic rhinitis: an evidence-based review", Drugs. 2007;67(6):887-901. doi: 10.2165/00003495-200767060-00005. PMID: 17428106. (also referred to as "Nayak and Langdon, 2007").
Skoner D.P. "Allergic rhinitis: definition, epidemiology, pathophysiology, detection, and diagnosis", J Allergy Clin Immunol. Jul. 2001;108(1 Suppl):S2-8. doi: 10.1067/mai.2001.115569. PMID: 11449200. ( also referred to as "Skoner, 2001").
Allergy and Asthma: Practical Diagnosis and Management, 2nd Ed., Mahmoudi (editor), Springer (publisher), Jun. 2, 2016, Chapter 6—Allergic Rhinitis: Diagnosis and Treatment, pp. 63-85 (also referred to as "Allergy and Asthma textbook").
Wenzel, et al., "Dupilumab in Persistent Asthma with Elevated Eosinophil Levels", New England Journal of Medicine, vol. 368:26, 2455-2466, May 21, 2013, Supplementary Appendix.
Vidal et al., "Evaluation of the Phadiatop™ test in the diagnosis of allergic sensitization in a general adult population", J Invest Allergol Clin Immunol, vol. 15(2), 124-130, 2005.
Corsica et al., "Allergen-specific immunoglobulin E and allergic rhinitis severity", AllerQy & Rhinoloav, vol. 8e1-e4, Mar. 1, 2017.
Bousquet, "Allergic Rhinitis and its Impact on Asthma (ARIA) in collaboration with the World Health Organization", J Allergy Clin Immunol, vol. 108: S147-S152.
Bousquet, "Allergic Rhinitis and its Impact on Asthma (ARIA) in collaboration with the World Health Organization", J Allergy Clin Immunol, vol. 108: S162-S170.
Bousquet, "Allergic Rhinitis and its Impact on Asthma (ARIA) in collaboration with the World Health Organization", J Allergy Clin Immunol, vol. 108: S198-S207.
Nials and Uddin, "Mouse models of allergic asthma: acute and chronic allergen challenge", Disease Models and Mechanisms, vol. 1, 213-220, 2008.
Clinical Study Record NCT01854047, Version 42, Nov. 27, 2015.
Study NCT02414854—Evaluation of Dupilumab in Patients with Persistent Asthma (Liberty Asthma Quest) (version 37) Record History I ver. 37: 2016-11-11 I NCT02414854 IClinicalTrials.gov Nov. 11, 2016.
Johansson. ImmunoCAP® Specific IgE test: an objective tool for research and routine allergy diagnosis. Expert Review of Molecular Diagnostics, 4(3), 273-279.9 Jan. 2014.
Bousquet et al. Allergic Rhinitis and its Impact on Asthma (ARIA). Allergy, 63: 8-160. Mar. 7, 2008.
Egan & Bunyavanich. Allergic rhinitis: the "Ghost Diagnosis" in patients with asthma. Asthma Res Pract. Sep 7;1 :8. Sep. 7, 2015.
Muraro et al. Precision medicine in patients with allergic diseases: Airway diseases and atopic dermatitis-PRACTALL document of the European Academy of Allergy and Clinical Immunology and the American Academy of Allergy, Asthma & Immunology, Journal of Allergy and Clinical Immunology, vol. 137, Issue 5, pp. 1347-1358. May 2016.
Vignola et al. Efficacy and tolerability of anti-immunoglobulin E therapy with omalizumab in patients with concomitant allergic asthma and persistent allergic rhinitis: SOLAR. Allergy, 59: 709-717. Jun. 4, 2004.
Juniper et al. Evaluation of impairment of health related quality of life in asthma: development of a questionnaire for use in clinical trials. Thorax 1992;47:76-83. 1992.
Dixon et al. Efficacy of nasal mometasone for the treatment of chronic sinonasal disease in patients with inadequately controlled asthma. Aug. 28, 2014.
Sheikh et al. House dust mite avoidance measures for perennial allergic rhinitis. Cochrane Database of Systematic Reviews, Issue 7, 1-22. 2010.
Sin and Togias, Proc Am Thorac Soc, 2011, 8:106-114.
Pomes et al., Curr Allergy Asthma Rep, 2016, 16:43.
Boulet and Boulay, Expert Review of Respiratory Medicine, 2011, 5(3) :377-393.
Borish, Am. J. Respir. Crit. Care Med., 2010, 181 :769-770.
Vatrella et al., Journal of Asthma and Allergy, 2014, 7:123-130.
Bachert et al., JAMA, 2016, 315(5):469-479.

(56) References Cited

OTHER PUBLICATIONS

Du et al., “Molecular Basis of Recognition of Human Osteopontin by 23C3, a Potential Therapeutic Antibody for Treatment of Rheumatoid Arthritis,” J. Mol. Biol. 382, 85-842 (2008) [doi:10.1016/j.jmb.2008.07.075].
Enclara Pharmacia, obtained from: https://enclarapharmacia.com/palliative-pearls/principles-of-pediatric-dosing#:~:text=Pediatric%20patients%20also%20have%20different,medication%20properties%20must%20be%20considered, (Year: 2020), 4 pages.
Dupixent Label provided by the FDA, “Highlights of Prescribing Information”, obtained from: https://www.accessdata.fda.gov/drugsatfda_docs/label/2020/761055s020lbl.pdf, Revised May 2020, 57 pages.
Dunne et al., “Extrapolation of Adult Data and Other Data in Pediatric Drug-Development Programs”, American Academy of Pediatrics, https://doi.org/10.1542/peds.2010-3487, Nov. 1, 2011, 3 pages.
Saitoh et al., “Study of total serum IgE, specific IgE antibody to Staphylococcal enterotoxins, and hemogramme in carriers of *Staphylococcus aureus*.,” Journal of Nutritional Science, vol. 43, No. 4, pp. 243-249 (Aug. 2002).
Takahashi, “Prediction of Adult Asthma Onset and Countermeasures Against Intractability,” Allergy, vol. 55, vol. 1, pp. 2-8 (2006).
Janda et al., “Ig Constant Region Effects on Variable Region Structure and Function,” Frontiers in Microbiology, vol. 7 Article 22, Feb. 2016.
Cooper et al., “Role of Heavy Chain Constant Domains in Antibody-Antigen Interaction,” The Journal of Immunology, vol. 150 No. 6, pp. 2231-2242 (Mar. 15, 1993).

* cited by examiner

| Week | -2 | 0 | 1 | 2 | 3 | 4 | 6 | 8 | 10 | 12 | 14 | 15 | 16 |
|---|---|---|---|---|---|---|---|---|---|---|---|---|---|
| | n | | | | | | | | | | | | |
| PBO | 27 | 27 | 26 | 25 | 26 | 22 | 16 | 14 | 15 | 14 | 12 | 13 | 12 |
| DPL 200 mg qw | 27 | 27 | 27 | 26 | 25 | 24 | 24 | 24 | 24 | 23 | 23 | 22 | 21 |

| Week | -2 | 0 | 1 | 2 | 3 | 4 | 6 | 8 | 10 | 12 | 14 | 15 | 16 |
|---|---|---|---|---|---|---|---|---|---|---|---|---|---|
| | | | | | | | n | | | | | | |
| PBO | 27 | 27 | 26 | 25 | 25 | 22 | 16 | 14 | 15 | 14 | 12 | 13 | 12 |
| DPL 200 mg qw | 27 | 27 | 27 | 26 | 24 | 24 | 24 | 24 | 24 | 23 | 23 | 22 | 21 |

| | Week | -2 | 0 | 1 | 2 | 3 | 4 | 6 | 8 | 10 | 12 | 14 | 15 | 16 |
|---|---|---|---|---|---|---|---|---|---|---|---|---|---|---|
| | | | | | | | n | | | | | | | |
| PBO | | 26 | 27 | 26 | 25 | 26 | 21 | 16 | 14 | 13 | 13 | 11 | 13 | 12 |
| DPL 200 mg qw | | 27 | 27 | 27 | 26 | 24 | 24 | 24 | 24 | 24 | 23 | 22 | 22 | 20 |

| | Placebo qw (n = 27) | | Dupilumab 200 mg qw (n = 27) | |
|---|---|---|---|---|
| Antigen-specific IgE | Baseline median (Q1,Q3),kU/L | Median % change (Q1,Q3),kU/L | Baseline median (Q1,Q3),kU/L | Median % change (Q1,Q3),kU/L |
| Cockroach German | 3 (0.7, 20.8) | 23 (8.9, 30.8) | 1 (0.3, 2.3) | -64 (-78.3, -18.5)* |
| Cladosporium | 2 (0.8, 4.8) | 36 (6.6, 65.4) | 1 (0.4, 9.4) | -62 (-75.0, -33.1)* |
| Staphylococcal enterotoxin A | 1 (0.5, 2.1) | 0 (-23.4, 26.8) | 1 (0.3, 1.7) | -61(-75.8, -50.4)** |
| Bermuda grass | 4 (1.0, 34.7) | 12 (-27.6, 82.3) | 2 (0.7, 3.8) | -60 (-66.9, -39.9)** |
| Silver birch | 27 (6.1, 56.5) | 28 (-47.5, 130.0) | 10 (0.5, 35.0) | -56 (-67.2, -41.8)* |
| Oak white | 15 (2.7, 38.7) | 5 (-33.6, 51.4) | 1 (0.3, 11.8) | -55 (-70.2, -39.8)** |
| Elm | 4 (1.1, 16.9) | -10 (-41.2, 22.9) | 1 (0.5, 4.5) | -54 (-66.7, -31.7)* |
| Johnson grass | 6 (0.8, 14.1) | -9 (-30.4, 17.4) | 1 (0.4, 1.9) | -52 (-71.6, -36.7)** |
| Cat dander | 22 (3.5, 51.6) | -25 (-36.8, 0.0) | 13 (2.2, 46.5) | -51 (-56.1, -33.3)* |
| Alder grey | 16 (2.0, 38.9) | 27 (-35.0, 131.7) | 7 (0.4, 22.4) | -50 (-70.3, -30.3)** |
| Timothy (Phleump.) | 27 (1.7, 54.1) | 21 (-7.7, 49.2) | 1 (0.7, 7.5) | -50 (-66.7, -34.0)** |
| White ash | 10 (1.2, 40.8) | 31 (-36.1, 39.5) | 1 (0.4, 16.2) | -53 (-65.4, -26.6)** |
| Dog dander | 25 (1.2, 95.8) | -1 (-31.8, 49.7) | 11 (3.2, 54.5) | -49 (-63.0, -40.0)* |
| Alternaria tenius | 1 (0.6, 5.3) | 8 (0.0, 89.1) | 1 (0.4, 4.3) | -46 (-61.5, -38.9)** |
| Ragweed short | 20 (4.7, 40.0) | -7 (-28.2, 0.0) | 2 (0.8, 13.2) | -41 (-59.4, -32.4)* |
| Dermatophagoides farinae | 63 (16.6, 200.0) | 0 (0.0, 78.5) | 66 (9.3, 200.0) | -39 (-63.1, -5.4)** |
| Staphylococcal enterotoxin B | 1 (0.4, 2.8) | -12 (-23.7, -1.7) | 1 (0.2, 2.9) | -33 (-58.3, -22.8)* |

*p<0.05, **p<0.01 vs placebo Q1,lower quartile of interquartile range; Q3, upper quartile of interquartile range;qw,once weekly

Figure 7

| | Placebo qw (n = 61) | | Dupilumab 100 mg q4w (n = 65) | | Dupilumab 300 mg q4w (n = 65) | |
|---|---|---|---|---|---|---|
| Antigen-specific IgE | Baseline median (Q1,Q3),kU/L | Median % change (Q1,Q3),kU/L | Baseline median (Q1,Q3),kU/L | Median % change (Q1,Q3),kU/L | Baseline median (Q1,Q3),kU/L | Median % change (Q1,Q3),kU/L |
| Candida albicans | 5 (0.3, 11.4) | 1 (-13.5, 34.6) | 3 (0.4, 12.0) | -18 (-39.5, 0.0)** | 5 (0.3, 11.5) | -43 (-58.8, -7.7)¶ |
| S.Enterotoxin A | 1 (0.2, 2.4) | 0 (-15.0, 28.4) | 1 (0.1, 2.0) | -32 (-48.1, -2.9)¶ | 1 (0.2, 1.9) | -33 (-56.4, 0.0)¶ |
| P. orbiculare/ M.furfur | 5 (0.1, 17.5) | 0 (-23.1, 9.2) | 8 (0.4, 15.3) | -17 (-33.3, 0.0) | 9 (0.1, 20.6) | -32 (-56.8, 0.0)¶ |
| Weed Mix 2 | 1 (0.2, 8.9) | 14 (-13.8, 75.4) | 2 (0.3, 14.1) | -19 (-45.8, 0.0)** | 2 (0.1, 11.0) | -30 (-57.3, 0.0)** |
| Cat dander | 4 (0.3, 22.7) | 0 (-16.7, 22.7) | 8 (0.2, 26.0) | -14 (-35.4, 0.0)* | 7 (0.3, 28.8) | -36 (-54.9, -4.4)¶ |
| Mold Mix 1 | 2 (0.3, 10.5) | 2 (-11.7, 30.3) | 2 (0.4, 9.9) | -10 (-32.9, 0.0)§ | 4 (0.8, 11.1) | -33 (-55.3, 0.0)¶ |
| S. Enterotoxin B | 0 (0.2, 1.5) | 0 (-11.1, 31.1) | 0 (0.1, 1.3) | -14 (-33.7,0.0)§ | 0 (0.1, 0.9) | -23 (-43.2, 0.0)¶ |
| D. farinae | 62 (1.5, 100.0) | 0 (0.0, 0.0) | 24 (1.1, 81.0) | 0 (-25.8, 0.0)* | 51 (0.3, 100.0) | -26 (-46.2, 0.0)** |
| D. pteronyssinus | 66 (0.2, 100.0) | 0 (-24, 0.0) | 52 (0.37, 100.0) | -8 (-35.3, 0.0)* | 58 (2.6, 100.0) | -11 (-43.5, 0.0)** |

Figure 8

| | Dupilumab 200 mg q2w (n = 61) | | Dupilumab 300 mg q2w (n = 64) | | Dupilumab 300 mg qw (n = 63) | |
|---|---|---|---|---|---|---|
| Antigen-specific IgE | Baseline median (IQR),kU/L | Median % change (IQR),kU/L | Baseline median (IQR),kU/L | Median % change (IQR),kU/L | Baseline median (IQR),kU/L | Median % change (IQR),kU/L |
| Candida albicans | 2 (0.3, 8.0) | -26 (-51.4, 0.0)¶ | 3 (0.5, 11.9) | -40 (-58.7, 0.0)¶ | 6 (0.2, 14.4) | -33 (-49.9, -0.0)¶ |
| S.Enterotoxin A | 0 (0.1, 1.0) | -24 (-47.2, 0.0)¶ | 1 (0.1, 1.5) | -37 (-58.3, 0.0)¶ | 1 (0.1, 1.5) | -14 (-45.8, 0.0)¶ |
| P. orbiculare/ M.furfur | 2 (0.2, 21.1) | -26 (-45.0, 0.0)§ | 4 (0.2, 21.1) | -41 (-61.5, -9.0)¶ | 8 (0.1, 19.5) | -23 (-44.6, 0.0)** |
| Weed Mix 2 | 1 (0.2, 4.1) | -29 (-48.1, 0.0)§ | 3 (0.2, 17.8) | -33 (-53.7, 0.0)§ | 0 (0.1, 10.0) | -24 (-47.9, 0.0)** |
| Cat dander | 6 (0.4, 23.1) | -31 (-42.5, 0.0)¶ | 8 (0.3, 37.1) | -25 (-41.2, 0.0)** | 4 (0.2, 3.0) | -27 (-45.5, 0.0)§ |
| Mold Mix 1 | 1 (0.2, 5.4) | -22 (-50.8, 0.0)¶ | 3 (0.3, 9.3) | -35 (-55.6, 0.0)¶ | 2 (0.2, 10.9) | -30 (-48.2, 0.0)¶ |
| S. Enterotoxin B | 0 (0.1, 1.0) | -18 (-47.6, 0.0)¶ | 1 (0.2, 1.8) | -28 (-48.1,-3.1)¶ | 0 (0.1, 1.0) | -3 (-39.7, 0.0)¶ |
| D. farinae | 8 (1.8, 100.0) | -32 (-46.2, 0.0)¶ | 28 (0.6, 100.0) | -19 (-52.4, 0.0)** | 6 (0.1, 100.0) | -5 (-51.3, 0.0)** |
| D. pteronyssinus | 28 (0.6, 98.1) | -18 (-44.6, 0.0)* | 18 (0.6, 92.2) | -22(-50.0, 0.0)** | 100 (4.8, 100.0) | 0 (-38.0, 0.0)* |

Figure 9

SEQUENCE LISTING

```
Sequence total quantity: 11
SEQ ID NO: 1            moltype = AA  length = 124
FEATURE                 Location/Qualifiers
source                  1..124
                        mol_type = protein
                        organism = synthetic construct
                        note = HCVR
SEQUENCE: 1
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVS                                                               124

SEQ ID NO: 2            moltype = AA  length = 112
FEATURE                 Location/Qualifiers
source                  1..112
                        mol_type = protein
                        organism = synthetic construct
                        note = LCVR
SEQUENCE: 2
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IK          112

SEQ ID NO: 3            moltype = AA  length = 8
FEATURE                 Location/Qualifiers
source                  1..8
                        mol_type = protein
                        organism = synthetic construct
                        note = HCDR1
SEQUENCE: 3
GFTFRDYA                                                           8

SEQ ID NO: 4            moltype = AA  length = 8
FEATURE                 Location/Qualifiers
source                  1..8
                        mol_type = protein
                        organism = synthetic construct
                        note = HCDR2
SEQUENCE: 4
ISGSGGNT                                                           8

SEQ ID NO: 5            moltype = AA  length = 18
FEATURE                 Location/Qualifiers
source                  1..18
                        mol_type = protein
                        organism = synthetic construct
                        note = HCDR3
SEQUENCE: 5
AKDRLSITIR PRYYGLDV                                                18

SEQ ID NO: 6            moltype = AA  length = 11
FEATURE                 Location/Qualifiers
source                  1..11
                        mol_type = protein
                        organism = synthetic construct
                        note = LCDR1
SEQUENCE: 6
QSLLYSIGYN Y                                                       11
```

-continued

```
SEQ ID NO: 7            moltype =   length =
SEQUENCE: 7
000

SEQ ID NO: 8            moltype = AA  length = 9
FEATURE                 Location/Qualifiers
source                  1..9
                        mol_type = protein
                        organism = synthetic construct
                        note = LCDR3
SEQUENCE: 8
MQALQTPYT                                                          9

SEQ ID NO: 9            moltype = AA  length = 451
FEATURE                 Location/Qualifiers
source                  1..451
                        mol_type = protein
                        organism = synthetic construct
                        note = HC aa1-124: HCVR; aa125-451: HC constant
SEQUENCE: 9
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFL  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 10           moltype = AA  length = 219
FEATURE                 Location/Qualifiers
source                  1..219
                        mol_type = protein
                        organism = synthetic construct
                        note = LC aa1-112: LCVR; aa113-219: LC constant
SEQUENCE: 10
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 11           moltype = AA  length = 207
FEATURE                 Location/Qualifiers
source                  1..207
                        mol_type = protein
                        organism = synthetic construct
                        note = hIL-4Ralpha
SEQUENCE: 11
MKVLQEPTCV SDYMSISTCE WKMNGPTNCS TELRLLYQLV FLLSEAHTCI PENNGGAGCV  60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQH                                      207
```

METHODS FOR PREVENTING OR TREATING ALLERGY BY ADMINISTERING AN IL-4R ANTAGONIST

CROSS-REFERENCE TO RELATED APPLICATIONS

This application is a continuation of U.S. patent application Ser. No. 16/329,184, filed Feb. 27, 2019, issued as U.S. Pat. No. 11,771,743 on Oct. 3, 2023, which is a U.S. National Stage application of PCT/US2017/049538, filed Aug. 31, 2017, which claims benefit of U.S. Provisional patent application No. 62/382,501, filed Sep. 1, 2016, and U.S. Provisional patent application No. 62/425,726, filed Nov. 23, 2016, which applications are incorporated herein by reference. To the extent appropriate, a claim of priority is made to each of the above-disclosed applications.

REFERENCE TO A SEQUENCE LISTING XML

The instant application contains a Sequence Listing which has been submitted electronically in XML format and is hereby incorporated by reference in its entirety. Said XML copy, created on Aug. 11, 2023, is named 40848_0077USC1_SL.xml and is 12,672 bytes in size.

FIELD OF THE INVENTION

The present invention relates to the prevention and/or treatment of allergy and allergic conditions. More specifically, the invention relates to the administration of interleukin-4 receptor (IL-4R) antagonists to prevent or treat allergy in a patient in need thereof.

BACKGROUND

Allergies and allergic diseases are serious medical conditions with consequences ranging from non-life threatening responses that resolve over time to life threatening effects such as anaphylaxis. Allergic reactions can result from contact or exposure to a variety of products such as certain food items, insect venom, plant-derived material (e.g., pollen), chemicals, drugs/medications, and animal dander. The pathophysiology of allergy is influenced by a complex interplay between Immunoglobulin E (IgE)-mediated sensitization, the immune system, and environmental factors. Current treatment options for allergies include avoidance, pharmacological symptom treatment and prophylaxis using allergen-specific immunotherapies (SIT). Unfortunately, these current treatment strategies are often inadequate, costly, impractical or involve significant risk. For example, avoidance of allergen is not always possible and can negatively impact on patient and caregiver quality of life. Immunotherapeutic approaches, on the other hand, involve deliberate administration of allergen to susceptible individuals and are therefore inherently risky with the potential for unwanted severe allergic reactions or anaphylaxis. Accordingly, an unmet need exists in the art for novel therapeutic approaches that prevent or treat allergies or allergic responses and reduce the risk of developing an allergic response.

BRIEF SUMMARY OF THE INVENTION

According to certain aspects of the present invention, methods are provided for preventing or treating allergy in a subject. Also included are methods of reducing the susceptibility to an allergic reaction or decreasing allergen sensitization in a subject. In certain embodiments, the invention provides for methods to reduce serum allergen-specific IgE levels in a subject. The methods of the present invention comprise administering to a subject in need thereof a pharmaceutical composition comprising a therapeutically effective amount of an interleukin-4 receptor (IL-4R) antagonist. In certain embodiments, the pharmaceutical composition is administered subcutaneously at a dose of 75-600 mg.

In certain embodiments, the present invention provides methods to prevent or treat allergy, wherein preventing or treating allergy comprises reducing the level of allergen-specific IgE. In certain embodiments, the subject in need thereof exhibits at least a 10%, at least 20%, at least 30%, at least 40%, or at least a 50% decrease in allergen-specific IgE upon administration of the IL-4R antagonist. In certain embodiments, the allergic reaction or susceptibility of a subject to an allergic reaction is triggered by allergen sensitization. In certain embodiments, the present invention provides methods to reduce or abrogate allergen sensitization.

In certain embodiments, the subject is sensitized to an allergen derived from one or more of the following sources including, but not limited to, Alder Grey, *Alternaria Tenuis*, Bermuda Grass, Silver Birch, Cat Dander, *Cladosporium*, Cockroach (German), *Dermatophagoides farinae* (mite), *D. pteronyssinus*, Dog Dander, Elm, Johnson Grass, White Oak, Ragweed Short, Mugwort Sage, Timothy (*Phleum*), White Ash, *Candida albicans, Malasezzia furfur, Pityrosporum orbiculare*, mold, *Staphylococcal enterotoxin* A, or *Staphylococcal enterotoxin* B. In certain embodiments, the subject is sensitized to an allergen derived from a food item selected from the group consisting of dairy, fish, shellfish, peanuts, tree nuts, fruit (e.g., melons), egg, wheat, and soy.

According to certain embodiments, the present invention provides methods for treating or preventing allergy or for reducing susceptibility to an allergic reaction in a subject, wherein the methods comprise sequentially administering to the subject about 50 mg to about 600 mg of an IL-4R antagonist as an initial dose followed by one or more secondary doses. In certain embodiments, the initial dose and the one or more secondary doses each comprise about 75 mg to about 300 mg of the IL-4R antagonist. In certain embodiments, the IL-4R antagonist is administered at an initial dose of 400 mg or 600 mg followed by one or more secondary doses wherein each secondary dose comprises 200 mg or 300 mg. According to this aspect of the invention, the pharmaceutical composition may be administered to the subject at a dosing frequency of, e.g., once a week, once in 2 weeks, once in 3 weeks or once in 4 weeks. In one embodiment, the IL-4R antagonist is administered at an initial dose of 400 mg followed by one or more secondary doses wherein each secondary dose comprises 200 mg and is administered weekly.

In certain embodiments, the invention provides methods to treat or prevent allergy, or to reduce susceptibility to an allergic reaction in a subject wherein the subject has a disease or disorder selected from the group consisting of atopic dermatitis, asthma, allergic rhinitis, eosinophilic esophagitis and food allergy. In one embodiment, the subject has moderate-to-severe atopic dermatitis.

Exemplary IL-4R antagonists that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R antagonist is an antigen-binding protein (e.g., antibody or antigen-binding fragment thereof) that binds the IL-4Ra chain and blocks signaling by IL-4, IL-13, or both IL-4 and IL-13. In one embodiment, the antibody or antigen-binding fragment thereof that specifically binds IL-4R comprises complementarity determining regions (CDRs) in a heavy chain variable region (HCVR)/light chain variable region (LCVR) sequence pair of SEQ ID NOs: 1/2. In certain embodiments, the antibody or antigen-binding fragment thereof comprises a heavy chain CDR (HCDR1) having amino acid sequence of SEQ ID NO: 3, a HCDR2 having amino acid sequence of SEQ ID NO: 4, a HCDR3 having amino acid sequence of SEQ ID NO: 5, a light chain CDR (LCDR1) having amino acid sequence of SEQ ID NO: 6, a LCDR2 having amino acid sequence LGS, and a LCDR3 having amino acid sequence of SEQ ID NO: 8. One such type of antigen-binding protein that can be used in the context of the methods of the present invention is an anti-IL-4Ra antibody such as dupilumab.

In some embodiments, the pharmaceutical composition is administered subcutaneously or intravenously to the subject.

In certain embodiments, the pharmaceutical composition is administered to the patient before, after or concurrent with a second therapeutic agent. In some embodiments, the second therapeutic agent is selected from the group consisting of another IL-4R inhibitor, an IgE inhibitor, a corticosteroid (e.g., topical corticosteroid or a systemic corticosteroid), a non-steroidal anti-inflammatory drug (NSAID), an anti-histamine, systemic immunotherapy, and IFNγ.

In certain embodiments, the present invention provides use of an IL-4R antagonist of the invention in the manufacture of a medicament to treat or reduce or prevent allergy or allergen sensitization in a patient.

Other embodiments of the present invention will become apparent from a review of the ensuing detailed description.

BRIEF DESCRIPTION OF THE FIGURES

FIG. 7 shows that dupilumab suppresses IgEs specific for a wide variety of allergens in serum after 16-week treatment as described in Example 2.

FIG. 8 shows suppression of IgEs specific for a wide variety of allergens in serum after 16-week treatment of placebo, dupilumab 100 mg every 4 weeks (q4w) or dupilumab 300 mg q4w, as described in Example 2. *P<0.05, **P<0.01, § P<0.001, ¶P<0.0001 vs placebo. *D. farinae, Dermatophagoides farinae; D. pteronyssinus, Dermatophagoides pteronyssinus; M. furfur, Malasezzia furfur; P. orbiculare; Pityrosporum orbiculare; S. enterotoxin* A/B, *Staphylococcal enterotoxin* A/B. Interquartile range: Q1, lowest quartile; Q3, upper quartile.

FIG. 9 shows suppression of IgEs specific for a wide variety of allergens in serum after 16-week treatment of dupilumab 200 mg every 2 weeks (q2w), 300 mg q2w, or 300 mg weekly (qw) as described in Example 2. *P<0.05, **P<0.01, § P<0.001, ¶P<0.0001 vs placebo. *D. farinae, Dermatophagoides farinae; D. pteronyssinus, Dermatophagoides pteronyssinus; M. furfur, Malasezzia furfur; P. orbiculare; Pityrosporum orbiculare; S. enterotoxin* A/B, *Staphylococcal enterotoxin* A/B. Interquartile range: Q1, lowest quartile; Q3, upper quartile.

DETAILED DESCRIPTION

Figure 1:
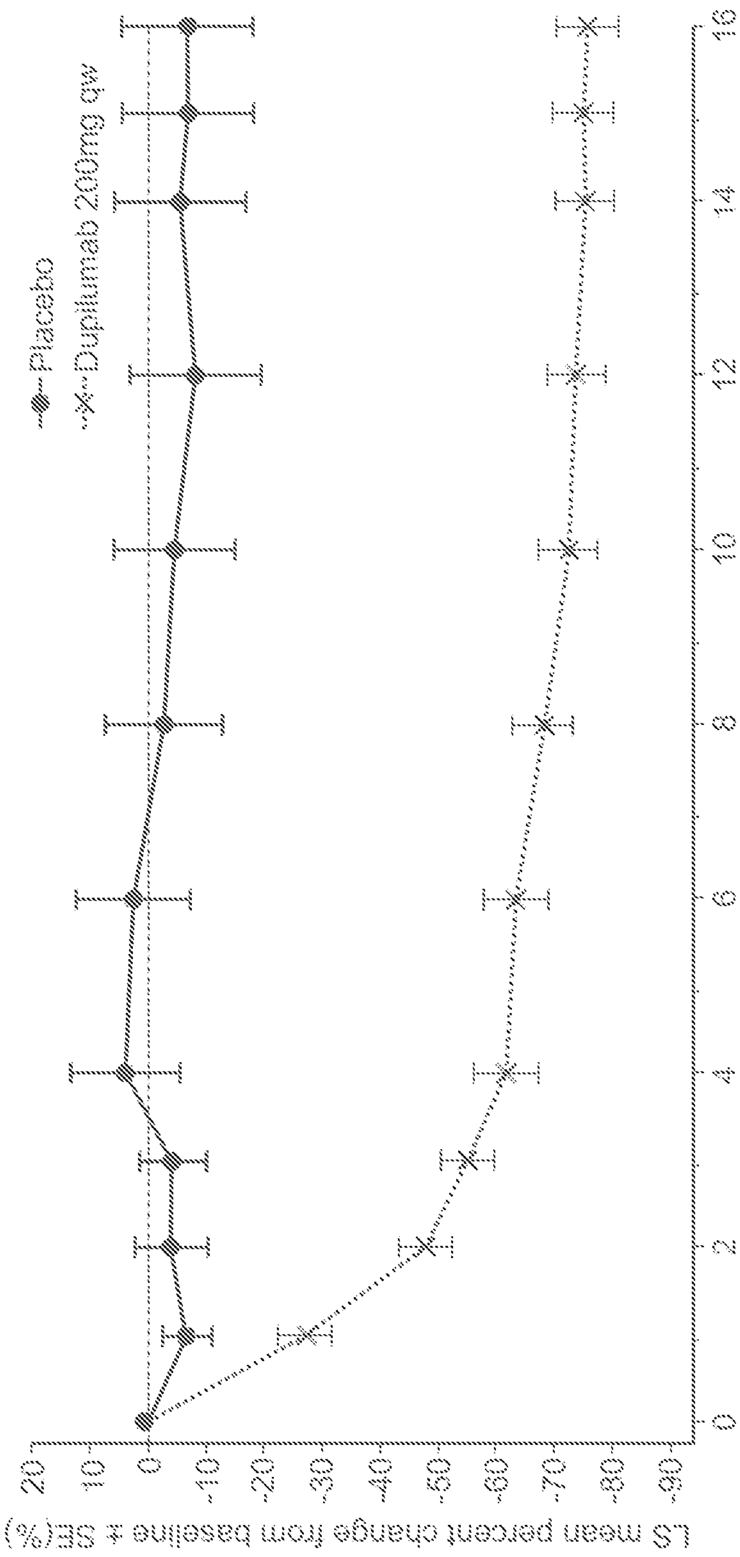
FIG. 1 shows least squares (LS) mean percent change in Eczema Area Severity Index (EASI) scores from baseline to week 16 in the study described in Example 1. *P<0.0001 vs placebo; qw, once weekly, SE, standard error.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

According to certain aspects, the present invention includes methods for preventing or treating allergy in a subject, wherein the methods comprise administering a therapeutically effective amount of an IL-4R antagonist to the subject in need thereof. As used herein, the terms "treat", "treating", or the like, mean to alleviate allergic symptoms, eliminate the causation of allergic symptoms either on a temporary or permanent basis, or to prevent or slow the appearance of allergic symptoms in a subject. As used herein, the terms "prevent", "preventing", or the like, refer to preventing development of allergy, an allergic reaction or an allergic condition. The term, as used herein, also includes reducing or abrogating allergen sensitization to prevent an allergic reaction. In some embodiments, the term refers to decreasing the level of serum allergen-specific IgE by at least 10%, at least 20%, at least 30%, at least 40%, or at least 50%, as compared to baseline, upon administration of an IL-4R antagonist as provided by the methods of the present invention.

The present invention includes methods which comprise administering to a subject in need thereof a therapeutic composition comprising an IL-4R antagonist. As used herein, the expression "a subject in need thereof" means a human or non-human animal that exhibits one or more symptoms or indicia of allergy or atopy, and/or who has been diagnosed with allergy to an allergen. In certain embodiments, the term "subject in need thereof" includes subjects that are at an increased risk for developing an allergy or an allergic response to an allergen. In certain embodiments, the term includes subjects that show allergen sensitization to one or more allergens. In certain embodiments, the methods of the present invention may be used to treat subjects that show elevated levels of one or more serum biomarkers including, but not limited to, total IgE, allergen-specific IgE, thymus and activation-regulated chemokine (TARC), pulmonary and activation-regulated chemokine (PARC), lactate dehydrogenase (LDH), and periostin. For example, the methods of the present invention comprise administering an IL-4R antagonist to patients with elevated levels of allergen-specific IgE. The terms "subject" and "patient" have been used interchangeably herein.

As used herein, the terms "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. Exemplary pollen allergens include, e.g., tree pollens such as birch pollen, cedar pollen, oak pollen, alder pollen, hornbeam pollen, *aesculus* pollen, willow pollen, poplar pollen, plantanus pollen, *tilia* pollen, *olea* pollen, Ashe juniper pollen, and Alstonia scholaris pollen. Other examples of allergens can be found elsewhere herein. The terms "allergen" and "antigen" are used interchangeably through the disclosure.

According to certain aspects, the present invention provides methods to reduce susceptibility to an allergic reaction in a subject, the methods comprising administering a therapeutically effective amount of an IL-4R antagonist to the subject in need thereof. In certain embodiments, the term "subject in need thereof" includes a subject that is susceptible to an allergic reaction or is at an increased risk for developing an allergic reaction to an allergen. In certain embodiments, a subject may be at an increased risk of developing an allergy or an allergic response to an allergen due to sensitization to said allergen. For example, the term includes subjects that show increased levels of serum IgE specific to one or more allergens ("allergen sensitization"). In the context of the present invention, the term "subject in need thereof", also includes subjects that have a disease or disorder selected from the group consisting of atopic dermatitis, asthma, allergic rhinitis, eosinophilic esophagitis and food allergy. The term "subject" also includes subjects with elevated levels of serum total and allergen-specific IgE, or serum chemokines (e.g., CCL17 or CCL27) that may have an increased risk of developing an allergic response. The present invention provides methods to decrease the risk of developing allergy or allergic response in susceptible subjects.

According to certain aspects, the present invention provides methods of reducing levels of serum allergen-specific IgE in a subject, the methods comprising administering a therapeutically effective amount of an IL-4R antagonist. In certain embodiments, the serum allergen-specific IgE levels are reduced by at least 10%, 20%, 30%, 40% or 50% as compared to the baseline following administration of the IL-4R antagonist.

Methods for detecting and/or quantifying a serum biomarker such as allergen-specific IgE or total IgE are known in the art; kits for measuring such a biomarker are available from various commercial sources; and various commercial diagnostic laboratories offer services which provide measurement of such biomarkers as well.

For example, Phadiatop™ is a commercially available variant of serum specific or antigen-specific IgE assay test that was introduced for the screening of allergic sensitization (Merrett et al 1987, Allergy 17: 409-416). The test provides for simultaneous testing for serum specific IgE to a mixture of relevant allergens causing common inhalant allergies. The test gives a qualitative result, either positive or negative depending upon a fluorescence response obtained. When a patient sample gives a fluorescence response higher than or equal to the reference, a positive test result is indicated. A patient sample with a lower fluorescence response indicates a negative test result. The present invention includes methods comprising selecting a subject who exhibits a positive test result and administering to the subject a therapeutically effective amount of an IL-4R antagonist.

The present invention also includes methods for determining whether a subject is a suitable subject for whom administration of a pharmaceutical composition comprising an IL-4R antagonist would be beneficial. For example, if an individual, prior to receiving a pharmaceutical composition comprising an IL-4R antagonist, exhibits a level of a serum biomarker (e.g., allergen-specific IgE) which signifies allergen sensitization, the individual is therefore identified as a suitable patient for whom administration of a pharmaceutical composition of the invention (a composition comprising an anti-IL-4R antibody) would be beneficial.

According to certain aspects of the invention, methods for preventing or treating allergy are provided which comprise: (a) selecting a subject who exhibits a level of IgE specific to at least one allergen prior to or at the time of treatment which signifies allergic sensitization; and (b) administering to the subject a pharmaceutical composition comprising a therapeutically effective amount of an IL-4R antagonist. In certain embodiments, the patient is selected by determining if the level of allergen-specific IgE is elevated. The level of allergen-specific IgE is determined or quantified by acquiring a sample from the patient for a biomarker assay known in the art. In certain other embodiments, a patient is selected by acquiring information relating to an elevated level of allergen-specific IgE from the patient. In certain embodiments of this aspect of the invention, the subject is selected on the basis of an elevated level of IgE or TARC or periostin.

As will be appreciated by a person of ordinary skill in the art, an increase or decrease in a serum biomarker can be determined by comparing (i) the level of the biomarker measured in a subject at a defined time point after administration of the IL-4R antagonist to (ii) the level of the biomarker measured in the patient prior to the administration of the IL-4R antagonist (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, 100 days, 150 days, or more after administration of the IL-4R antagonist.

According to certain particular embodiments of the present invention, a subject may exhibit a decrease in the level of serum IgE specific to one or more allergens following administration of a pharmaceutical composition comprising an IL-4R antagonist (e.g., an anti-IL-4R antibody). For example, at about day 8, day 15, day 22, day 25, day 29, day 36, day 43, day 50, day 57, day 64, day 71, day 85, or day 112, following administration of one or more doses of a pharmaceutical composition comprising about 75, 150, 200 or 300 mg of an anti-hIL-4R antibody (e.g., dupilumab), the subject, according to the present invention, may exhibit a decrease in allergen-specific IgE of about 1%, 2%, 5%, 10%, 15%, 20%, 25%, 30%, 35%, 40%, 45%, 50%, 55%, 60%, 65%, 70%, 75%, 80%, 85%, 90% or more from baseline (wherein "baseline" is defined as the level of allergen-specific IgE in the subject just prior to the first administration).

Interleukin-4 Receptor Antagonists

The methods of the present invention comprise administering to a subject in need thereof a therapeutic composition comprising an interleukin-4 receptor (IL-4R) antagonist. As used herein, an "IL-4R antagonist" (also referred to herein as an "IL-4R inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor.

Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

According to certain exemplary embodiments of the present invention, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized.

The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (iX) $V_L$-$C_H2$; (X) $V_L$-$C_H3$; (Xi) $V_L$-$C_H1$-$C_H2$; (Xii) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence LGS; and the LCDR3 comprises the amino acid sequence of SEQ ID NO: 8. In some embodiments, the anti-IL-4R antibody or antigen-binding fragment thereof comprises an HCVR comprising SEQ ID NO: 1 and an LCVR comprising SEQ ID NO: 2. According to certain exemplary embodiments, the methods of the present invention comprise the use of the anti-IL-4R antibody comprising HCDR1-HCDR2-HCDR3-LCDR1-LCDR2-LCDR3 amino acid sequences (of) SEQ ID NO: 3-SEQ ID NO: 4-SEQ ID NO: 5-SEQ ID NO: 6-LGS-SEQ ID NO: 8 (referred to and known in the art as "dupilumab"), or a bioequivalent thereof. In certain embodiments, the methods of the present invention comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody known as dupilumab. According to certain exemplary embodiments, the methods of the present invention comprise the use of dupilumab, or a bioequivalent thereof. The term "bioequivalent", as used herein, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In the context of the invention, the term refers to antigen-binding proteins that bind to IL-4R which do not have clinically meaningful differences with dupilumab in their safety, purity and/or potency.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or MEDI 9314, or any of the anti-IL-4Rα antibodies as set forth in U.S. Pat. No. 7,186,809, 7,605,237, 7,638,606, 8,092,804, 8,679,487, or 8,877,189.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which comprise administering an IL-4R antagonist to a patient, wherein the IL-4R antagonist (e.g., an anti-IL-4R antibody) is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351). Specific exemplary doses of anti-IL4R antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in U.S. Pat. No. 8,945,559.

Dosage

The amount of IL-4R antagonist (e.g., anti-IL-4R antibody) administered to a subject according to the methods of the present invention is, generally, a therapeutically effective amount. As used herein, the phrase "therapeutically effective amount" means an amount of IL-4R antagonist that results in one or more of: (a) prevention of allergy; (b) treatment of or reduction in the severity of an allergic reaction; (c) reduction in the level of serum allergen-specific IgE; (d) reduction of allergen sensitization; and/or (e) reduction in susceptibility to an allergic reaction.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 75 mg, 100 mg, 150 mg, 200 mg, or 300 mg of an anti-IL-4R antibody is administered to a subject.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods of the present invention, according to certain embodiments, comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. The term "in combination with" also includes sequential or concomitant administration of IL-4R antagonist and a second therapeutic agent.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" or with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a tumor necrosis factor (TNF) antagonist, an IL-8 antagonist, an IL-9 antagonist, an IL-17 antagonist, an IL-5 antagonist, an IgE antagonist, a CD48 antagonist, an IL-31 antagonist (including, e.g., as set forth in U.S. Pat. No. 7,531,637), a thymic stromal lymphopoietin (TSLP) antagonist (including, e.g., as set forth in US 2011/027468), interferon-gamma (IFNγ) antibiotics, topical corticosteroids, tacrolimus, pimecrolimus, cyclosporine, azathioprine, methotrexate, cromolyn sodium, proteinase inhibitors, systemic corticosteroids, systemic immunotherapy, anti-histamines, or combinations thereof. In certain embodiments, the pharmaceutical composition comprising an anti-IL4R antagonist is administered to a subject in conjunction with a non-pharmaceutical therapy such as ultraviolet (UV) light therapy.

Administration Regimens

The present invention includes methods comprising administering to a subject a pharmaceutical composition comprising an IL-4R antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-4R antibody, once a week dosing at an amount of about 75 mg, 150 mg, 200 mg, or 300 mg, can be employed.

According to certain embodiments of the present invention, multiple doses of an IL-4R antagonist may be administered to a subject over a defined time course. The methods according to this aspect of the invention comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a patient with AD at a loading dose of about 400 mg or about 600 mg followed by one or more maintenance doses of about 75 mg to about 300 mg. In one embodiment, the initial dose and the one or more secondary doses each include 50 mg to 600 mg of the IL-4R antagonist, e.g., 100 mg to 400 mg of the IL-4R antagonist, e.g., 100 mg, 150 mg, 200 mg, 250 mg, 300 mg, 400 mg or 500 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of the IL-4R antagonist.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

The methods according to this aspect of the invention may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial Investigating Efficacy of Dupilumab in Adult Patients with Moderate-to-Severe AD

Study Design and Objectives

This was a 32-week randomized, double-blind, placebo-controlled, parallel group study to assess the safety, efficacy, biomarker profile, functional concentrations and immunogenicity of dupilumab administered weekly for 16 consecutive weeks to adult patients with moderate-to-severe AD. Dupilumab is a fully human anti-IL-4R antibody comprising a heavy chain comprising the amino acid sequence of SEQ ID NO: 9 and a light chain comprising the amino acid sequence of SEQ ID NO: 10; an HCVR/LCVR amino acid sequence pair comprising SEQ ID NOs: 1/2; and heavy and light chain CDR sequences comprising the amino acid sequences (of) SEQ ID NO: 3, SEQ ID NO: 4, SEQ ID NO: 5, SEQ ID NO: 6, LGS, AND SEQ ID NO: 8.

Eligible patients were randomized in a 1:1 ratio to receive subcutaneous (SC) dupilumab or SC placebo. Randomization was stratified by disease severity (moderate vs. severe AD). After providing informed consent, patients were assessed for study eligibility at the screening visit. Patients who met eligibility criteria underwent day 1/baseline assessments, randomization and received a loading dose (400 mg SC of study drug) with subsequent weekly injections of study drug (200 mg SC) from week 1 through week 15. During this time, patients underwent weekly assessments, most through clinical visits, but some through telephone contact. Depending upon the patient's preference and capabilities, patients and/or caregivers were trained at the study site on injecting the study drug at the first 5 treatment visits (visits 2, 3, 4, 5 and 6) and subsequently administered the study drug outside the clinic at visits 7, 9, 11, 13 and 15, which required only a telephone contact. Safety, laboratory and clinical effect assessments were performed at specific clinic visits. The end of treatment period visit occurred at week 16 after the last dose of study drug, when the primary endpoint was assessed. Follow-up visits occurred every 2 weeks from week 18 through week 32. The end of study visit occurred at week 32.

Rescue treatment for AD (medication and/or phototherapy) was provided to the patients, if necessary. Patients who needed rescue treatment were discontinued from the study treatment, but continued to follow the schedule of study assessments. Efficacy measurements (e.g., IGA, EASI, etc.) were obtained before any rescue treatment was administered.

Samples for clinical chemistry and hematology, drug concentration and anti-drug antibodies were collected at various time-points during the study. In addition, 1 sample for DNA analysis and multiple samples for RNA analysis were collected.

Treatment assignment was allocated randomly, to avoid predisposition in assigning patients to a particular treatment group and to minimize systematic differences between treatment groups with respect to baseline variables that could affect the outcome. The double-blind design was intended to minimize any potential bias in clinical assessments and patient reported outcomes resulting from investigator's or patient's knowledge of treatment allocation. The placebo arm provided a reliable reference of any apparent effects of the study treatment. Patients assigned to the dupilumab arm received 200 mg once weekly (qw) after a 400 mg loading dose on day 1. Study treatment was administered for 16 weeks so as to stabilize systemic concentrations of functional dupilumab. After the treatment, all patients were followed for 16 weeks (i.e., approximately 5 half-lives) to ensure that dupilumab clearance was virtually complete (plasma concentrations below the lower limit of quantification) before the end of study visit.

The primary objective of the study was to assess the efficacy of dupilumab, compared to placebo, in adult patients with moderate-to-severe AD.

The secondary objectives of the study were: (1) to assess the safety of dupilumab, compared to placebo; (2) to assess the concentration of dupilumab; and (3) to assess the potential anti-drug antibody response to dupilumab, compared to placebo, in adult patients with moderate-to-severe AD.

The exploratory objectives were: (1) to assess the effect of dupilumab on epidermal hyperplasia; (2) to assess the pharmacodynamic (PD) effect of dupilumab on biomarkers over time; and (3) to assess the predictive value of thymus and activation-regulated cytokine (TARC) on the EASI response.

The target population included adults with moderate-to-severe AD which was not adequately controlled with topical medications or where the topical treatment was inadvisable (due to, e.g., side effects or safety risks). Eligible patients were randomized in a 1:1 ratio to receive subcutaneous (SC) dupilumab or SC placebo. Randomization was stratified by disease severity (moderate vs. severe AD). Patients received a loading dose (400 mg SC) of study drug on day 1, followed by weekly injections of study drug (200 mg SC) from week 1 through week 15. Patients were required to apply a topical emollient twice daily from day −7 through day 8. Safety, laboratory and clinical effect assessments were performed at specified clinic visits. Samples for clinical chemistry and hematology, drug concentration and anti-drug antibodies were collected at various time-points throughout the study. In addition, 1 sample for DNA analysis and multiple samples for RNA analysis were collected. The end of treatment period visit occurred at week 16, 1 week after the last dose of study drug, when the primary endpoint was assessed. Follow-up visits occurred every 2 weeks from week 18 through week 32. The end of study visit occurred at week 32.

The primary endpoint in the study was the percent change in EASI score from baseline to week 16. The secondary endpoints included: (1) proportion of patients achieving IGA 0 (clear) or 1 (almost clear) at week 16; (2) proportion of patients achieving IGA score reduction of ≥2 at week 16; (3) absolute and percent change from baseline in pruritus scores (NRS and 4-point categorical scale); (4) absolute change in EASI scores from baseline to week 16; (5) absolute and percent change in SCORAD scores from baseline to week 16; (6) proportion of patients achieving EASI-50, EASI-75 and EASI-90 (50, 75 and 90% reduction from baseline in EASI score) at week 16; (7) proportion of patients achieving SCORAD-50, SCORAD-75 and SCORAD-90 (50, 75 and 90% reduction from baseline in SCORAD score) at week 16; (8) absolute and percent change from baseline in POEM scores; (9) changes from baseline in GISS components (erythema, infiltration/population, excoriations, and lichenification); (10) changes from baseline in GISS cumulative score; (11) incidence of TEAEs from baseline through week 32; and (12) dupilumab serum concentrations overtime from baseline through week 32.

The exploratory endpoints include: (1) the proportion of patients with a histological response consisting of significantly decreased epidermal hyperplasia in lesional skin and defined as ≥40% reduction from baseline in epidermal thickness and/or reversal of K16 expression by immunohistochemistry; (2) change in TARC from baseline through week 16; (3) change in IgE from baseline through week 16; (4) change in allergen-specific IgE through week 16; and (5) correlation of baseline TARC and IgE on EASI response.

Patient Selection

The target population included adults with moderate-to-severe AD which was not adequately controlled with topical medications or for whom topical treatment is otherwise inadvisable (due to e.g., side effects or safety risks).

Inclusion Criteria: A patient had to meet the following criteria to be eligible for inclusion in the study: (1) male or female, 18 years or older; (2) chronic AD, that had been present for at least 3 years before the screening visit; (3) EASI score ≥12 at the screening visit and ≥16 at the baseline visit; (4) IGA score 3 (on the 0-4 IGA scale) at the screening and baseline visits; (5) ≥10% BSA of AD involvement at the screening and baseline visits; (6) patients with documented recent history (within 6 months before the screening visit) of inadequate response to outpatient treatment with topical medications or for whom topical treatments were otherwise inadvisable (e.g., because of important side effects or safety risks) [For the purpose of this protocol, inadequate response represented failure to achieve and/or maintain remission or a low disease activity state (e.g., IGA 0=clear to 2=mild) despite treatment with topical corticosteroids of medium to high potency (±topical calcineurin inhibitors as appropriate]. To assess inadequacy of response to intensive treatment, topical treatment was applied daily for at least 28 days or for the maximum duration recommended by the product prescribing information (e.g., 14 days for super-potent topical corticosteroids), whichever was shorter. Following intensive daily treatment, inadequacy of response was determined based on failure to maintain a low disease activity state despite applications of topical medications on a less intensive maintenance schedule (i.e., 2 days per week). Important side effects or safety risks that outweighed the potential treatment benefits (e.g., hypersensitivity reactions, significant skin atrophy, systemic effects, etc., or imminence thereof), as assessed by the investigator or by patient's treating physician. Acceptable documentation included contemporaneous chart notes that recorded prescription of topical corticosteroids and/or topical calcineurin inhibitors, and treatment outcome, investigator documentation based on communication with patient's treating physician, or medical history provided by the patient in the event that other forms of documentation were not available (e.g., patient had not seen a physician for AD in the last 6 months)]; (7) patients must have applied a stable dose of topical emollient (moisturizer) twice daily for at least 7 days before the baseline visit; (8) willing and able to comply with all clinic visits and study-related procedures; (9) able to understand and complete study-related questionnaires; and (10) provide signed informed consent.

Exclusion Criteria: The following were the exclusion criteria for the study: (1) prior participation in a clinical trial with dupilumab; (2) treatment with an investigational drug within 8 weeks or within 5 half-lives (if known), whichever was longer, before the baseline visit; (3) the following treatments within 4 weeks before the baseline visit, or any condition that, in the opinion of the investigator, would require such treatment(s) during the first 4 weeks of study treatment—systemic corticosteroids, immunosuppressive/immunomodulating drugs (e.g., cyclosporine, mycophenolate-mofetil, IFNγ, Janus kinase (JAK) inhibitors, azathioprine or methotrexate), or phototherapy for AD; (4) treatment with topical corticosteroids, tacrolimus and/or pimecrolimus within 1 week before the baseline visit; (5) treatment with biologics as follows: any cell-depleting agents including but not limited to rituximab: within 6 months before the baseline visit, or until lymphocyte and CD 19+ lymphocyte count returned to normal, whichever was longer; infliximab, adalimumab, golimumab, certolizumab pegol, abatacept, etanercept, anakinra: within 16 weeks before the baseline visit for any indication, or within 5 years for dermatological indications, other biologics: within 5 half-lives (if known) or 16 weeks, whichever was longer, before the baseline visit; (6) initiation of treatment of AD with prescription moisturizers or moisturizers containing additives such as ceramide, hyaluronic acid, urea, or filaggrin during the screening period (patients could continue using stable doses of such moisturizers if initiated before the screening visit); (7) regular use (more than 2 visits per week) of a tanning booth/parlor within 4 weeks before the baseline visit; (8) planned or anticipated use of any prohibited medications and procedures during study treatment; (9) treatment with a live (attenuated) vaccine within 12 weeks before the baseline visit; (10) chronic or acute infection requiring treatment with systemic antibiotics, antivirals, antiparasitics, antiprotozoals, or antifungals within 4 weeks before the screening visit, or superficial skin infections within 1 week before the screening visit; (11) known or suspected immunosuppression, including history of invasive opportunistic infections (e.g., tuberculosis, histoplasmosis, listeriosis, coccidioidomycosis, pneumocystosis, aspergillosis) despite infection resolution, or otherwise recurrent infections of abnormal frequency, or prolonged infections suggesting an immune-compromised status; (12) known history of human immunodeficiency virus (HIV) infection or HIV seropositivity at the screening visit; (13) positive or indeterminate hepatitis B surface antigen (HBsAg), hepatitis B core antibody (HBcAb), or hepatitis C antibody at the screening visit; (14) elevated transaminases (ALT and/or AST) more than 3 times the upper limit of normal (>3 xULN) at the screening visit; (15) history of clinical endoparasitosis within 12 months before the baseline visit, other than treated vaginal trichomoniasis; (16) presence of skin comorbidities that could interfere with study assessments; (17) history of malignancy within 5 years before the baseline visit, except completely treated in situ carcinoma of the cervix, and completely treated and resolved non-metastatic squamous or basal cell carcinoma of the skin; (18) history of non-malignant lymphoproliferative disorders; (19) high risk of parasite infection, such as residence within or recent travel (within 12 months before the baseline visit) to areas endemic for endoparasitoses, where the circumstances were consistent with parasite exposure (e.g., extended stay, rural or slum areas, lack of running water, consumption of uncooked, undercooked, or otherwise potentially contaminated food, close contact with carriers and vectors, etc.), unless subsequent medical assessments (e.g., stool exam, blood tests, etc.) had ruled out the possibility of parasite infection/infestation; (20) history of alcohol or drug abuse within 2 years before the screening visit; (21) severe concomitant illness(es) that, would adversely affect the patient's participation in the study. Examples included, but were not limited to patients with short life expectancy, patients with uncontrolled diabetes (HbA1c≥9%), patients with cardiovascular conditions (e.g., stage III or IV cardiac failure according to the New York Heart Association classification), severe renal conditions (e.g., patients on dialysis) hepatobiliary conditions (e.g., Child-Pugh class B or C), neurological conditions (e.g., demyelinating diseases), active major autoimmune diseases (e.g., lupus, inflammatory bowel disease, rheumatoid arthritis, etc.), other severe endocrinological, gastrointestinal, metabolic, pulmonary, or lymphatic diseases; (22) any other medical or psychological condition including relevant laboratory abnormalities at screening that suggested a new and/or insufficiently understood disease, could present an unreasonable risk to the study patient as a result of his/her participation in this clinical trial, could make patient's participation unreliable, or interfere with study assessments. This included hypersensitivity to local anesthetics, bleeding disorders, treatment with anticoagulants or other conditions that could make the biopsy procedure inadvisable; (23) planned major surgical procedure during the patient's participation in this study; (24) pregnant or breast-feeding women or women planning to become pregnant or breastfeed during the study; and (25) women unwilling to use adequate birth control, if of reproductive potential and sexually active.

Study Treatments

Patients received a subcutaneous loading dose of 400 mg dupilumab on day 1 followed by 200 mg weekly (qw) from week 1 through week 15. Patients on placebo received a loading dose at day 1 followed by weekly subcutaneous dose of placebo from week 1 to week 15. Patients were required to apply a topical emollient twice daily from day −7 through day 8.

Procedures and Assessments

The efficacy of dupilumab in this population was assessed by AD disease severity scores, quality of life (QOL) questionnaires, pruritus assessments, and patient-reported outcomes. AD severity scores included AD-associated clinical parameters such as Eczema Area and Severity Index (EASI), Investigator's Global Assessment (IGA), Pruritus Numerical Rating Scale (NRS), Body Surface Area (BSA), 5-D Pruritus, SCORing Atopic Dermatitis (SCORAD), Patient Oriented Eczema Measure (POEM), and Global Individual Sign Score (GISS), which are described in US Patent Application Publication No. US2014/0072583 (incorporated by reference herein in its entirety). Quality of Life (QOL) questionnaires included Patient Global Assessment of Disease Status, Dermatology Life Quality Index (DLQI), POEM, EQ-5D, Itchy QoL, and Hospital Anxiety and Depression Scale (HADS), described in US2014/0072583 (incorporated by reference in its entirety). Skin barrier function tests, photographs of the AD area and skin swab samples for exploratory microbiome analyses were also collected. The safety of dupilumab in this population was assessed by evaluating TEAEs, detailed medical history, thorough physical examination, vital signs, electrocardiogram (ECG), and clinical laboratory testing. Concomitant medications and procedures were collected from time of informed consent to the end of the study. Blinded safety data was reviewed on an ongoing basis. Blood samples were collected for drug concentration and anti-dupilumab antibody levels at pre-determined time points. Research samples and samples for exploratory biomarker analysis were collected. Skin biopsy samples were also collected for exploratory biomarker analysis.

Statistical Analyses

Primary and secondary continuous variables were analyzed using an analysis of covariance (ANCOVA) model with treatment and randomization strata (moderate vs. severe), and relevant endpoint baseline values as covariates. The efficacy data were set to missing after rescue medication was used or after the patient discontinued from the study. Then all missing values were imputed using the last observation carried forward (LOCF) method. EASI and pruritus NRS were reported as least squares (LS) mean (standard error [SE]) percent changes from baseline to Week 16, derived from the LOCF approach.

Results

Patient Disposition and Baseline Characteristics: 54 patients were randomized to placebo (n=27) or dupilumab 200 mg qw (n=27). Baseline demographics and clinical characteristics were balanced between the treatment groups (Table 1). More than 75% of patients had used prior medications including antihistamines, topical corticosteroids (of groups I, II and III, by potency), and drugs for obstructive airway diseases. A higher proportion of patients on placebo used corticosteroids than patients on dupilumab.

TABLE 1

Baseline patient demographics and clinical characteristics by treatment group

| Variable | Placebo (n = 27) | Dupilumab 200 mg (n = 27) |
|---|---|---|
| Age, median (IQR), years | 43 (20, 82) | 35 (18, 71) |
| Male sex, n (%) | 14 (51.9) | 16 (59.3) |
| AD duration, mean ± SD, years | 35.4 ± 16.3 | 26.3 ± 17.21 |
| BSA, mean ± SD, % | 54.5 ± 26.91 | 53.8 ± 29.72 |
| EASI score (0-72), mean ± SD | 34.2 ± 14.59 | 33.4 ± 15.41 |
| Total SCORAD score (0-103), mean ± SD | 65.1 ± 13.36 | 64.2 ± 17.67 |
| Peak Pruritus NRS score (0-10), mean ± SD | 7.4 ± 2.04 | 7.1 ± 2.42 |
| IGA score (0-4), n (%) | | |
| Score = 3 (moderate) | 13 (48.1) | 14 (51.9) |
| Score = 4 (severe) | 14 (51.9) | 13 (48.1) |

Figure 2:
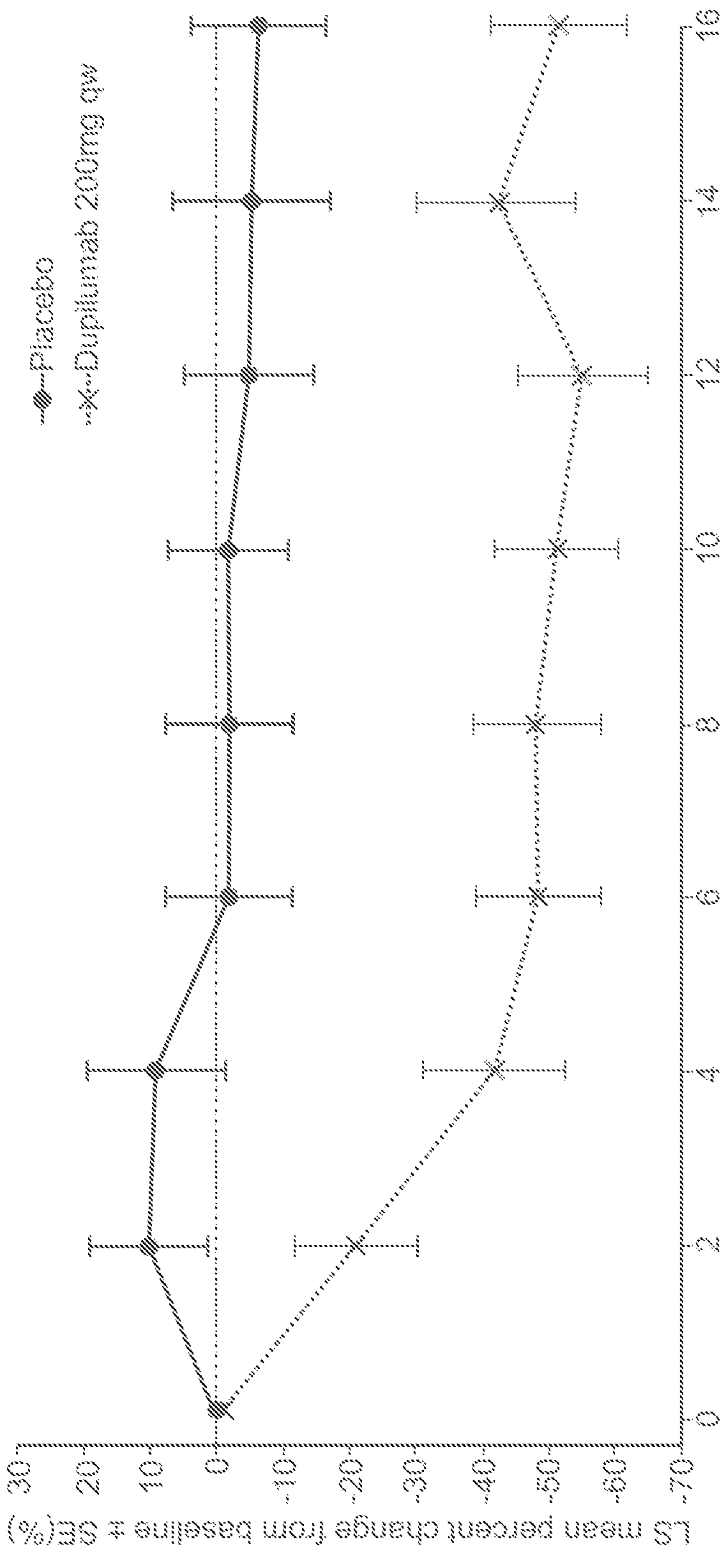
FIG. 2 shows LS mean percent change in peak weekly pruritus numerical rating scale (NRS) scores from baseline to week 16 in the study described in Example 1. *P<0.01 vs placebo; LS, least squares.

Efficacy: Dupilumab treatment significantly improved (reduced) EASI scores from baseline to Week 16 compared with placebo (SE): −75.2% (8.15) vs −5.8% (8.16); P<0.0001 (FIG. 1). Peak weekly pruritus NRS was also significantly reduced from baseline to Week 16 with dupilumab treatment compared with placebo (SE): −51.5% (10.2) vs −6.3% (10.0); P=0.0027 (FIG. 2). A greater proportion of the dupilumab group patients [14/27 (51.9%)] achieved a reduction in IGA of ≥2 points by week 16, compared with the placebo group [1/27 (3.7%)]. 37% of dupilumab group patients achieved a score of 0 (clear) or 1 (almost clear) by week, compared with no patient in the placebo group. The proportions of patients who achieved reduction in their EASI score by week 16 were consistently greater in the dupilumab group, than in the placebo group, as evidenced by the proportions of patients with EASI-50 (21/27 [77.8%] dupilumab versus 6/27 [22.2%] placebo, p<0.0001), EASI-75 (18/27 [66.7%] dupilumab versus 4/27 [14.8%] placebo, p=0.0001), and EASI-90 (9/27 [33.3%] dupilumab versus 0/27 [0%] placebo, p=0.0011). The LS mean (±SE) percentage change in SCORAD score from baseline to week 16 was consistent with the change in absolute mean SCORAD (−54.8±5.40% dupilumab versus −8.2±5.41%, p<0.0001). The proportions of patients who achieved a 50% SCORAD reduction (SCORAD-50) by week 16 were observed to be greater in the dupilumab group than in placebo group (15/27 [55.6%] dupilumab versus 2/27 [7.4%] placebo, p=0.0002). The dupilumab group showed LS mean (±SE) percentage decrease from baseline in BSA involvement from baseline to week 16 of −69.0±12.61%, whereas the placebo group showed an increase of 13.6±12.61%.

Safety: Dupilumab was safe and well tolerated and had an acceptable safety profile. 23/27 (85.2%) patients in the dupilumab group and 24/27 (88.9%) patients in the placebo group had at least 1 TEAE. Serious TEAEs were reported in 3/27 (11.1%) patients in the placebo group and none were reported in the dupilumab group. Most TEAEs were of mild or moderate severity. Common TEAEs (by Medical Dictionary for Regulatory Activities [MedDRA] Preferred Term) included nasopharyngitis (dupilumab: 3/27 [11.1%] of patients; placebo: 5/27 [18.5%] of patients), upper respiratory tract infection (4/27 [14.8%] and 4/27 [14.8%], respectively), viral upper respiratory tract infection (3/27 [11.1%] and 2/27 [7.4%], respectively) and injection-site reactions (by MedDRA High Level Term; 5/27 [18.5%] and 1/27 [3.7%], respectively).

Example 2: Biomarker Analyses

A. Study A

In Study "A", serum biomarkers were measured in samples from a clinical trial involving subjects with moderate-to-severe atopic dermatitis (AD). Subjects with AD were administered 16 weekly doses of either dupilumab (200 mg) or placebo; patients on dupilumab received a loading dose of 400 mg on day 1. AD-associated serum biomarkers such as thymus and activation-regulated chemokine (TARC), pulmonary and activity-regulated chemokine (PARC), periostin, lactate dehydrogenase (LDH), eosinophil, total IgE, and antigen-specific IgE are described in US Patent Application Publication No. US2014/0072583 (incorporated by reference in its entirety).

Serum biomarkers were measured at various time points between screening and Week 32 and included: Serum TARC (Human CCL17/TARC Quantikine ELISA kit; R&D Systems, Minneapolis, MN, USA) and periostin (Human Periostin/OSF-2 DuoSet 15 Plate; R&D Systems). Total IgE and allergen-specific IgEs in serum were measured by ImmunoCap assay (ImmunoCAPR Fluorescent Enzyme Immunoassay; Thermo Scientific, Uppsala, Sweden). Allergen IgE panels were established for common aeroallergens for the region together with *S. aureus* enterotoxin A and B IgEs. For allergen-specific IgE, the lower limit of quantitation was 0.10 kU/L; a level ≥0.35 kU/L was considered evidence of allergen sensitization.

Exploratory variables, serum biomarkers TARC, PARC, periostin and total IgE were plotted as mean (SE) percent changes from baseline; antigen-specific IgEs abundance were reported as median (interquartile range [IQR]) percent change from baseline. Data were set to missing after rescue medication. Variables were not adjusted for multiplicity and thus nominal p values are provided.

TABLE 2

Baseline Biomarker Scores

| Variable | Placebo (n = 27) | Dupilumab 200 mg (n = 27) |
|---|---|---|
| Serum TARC, mean (SD), pg/mL | 11360 (24670) | 7722 (13590) |
| Serum PARC, mean (SD), ng/mL | 206 (188) | 168 (127) |
| Serum periostin, mean (SD), ng/mL | 147 (100) | 154 (117) |
| Serum total IgE, mean (SD), IU/mL | 5641 (4706) | 3868 (4248) |

Figure 3:
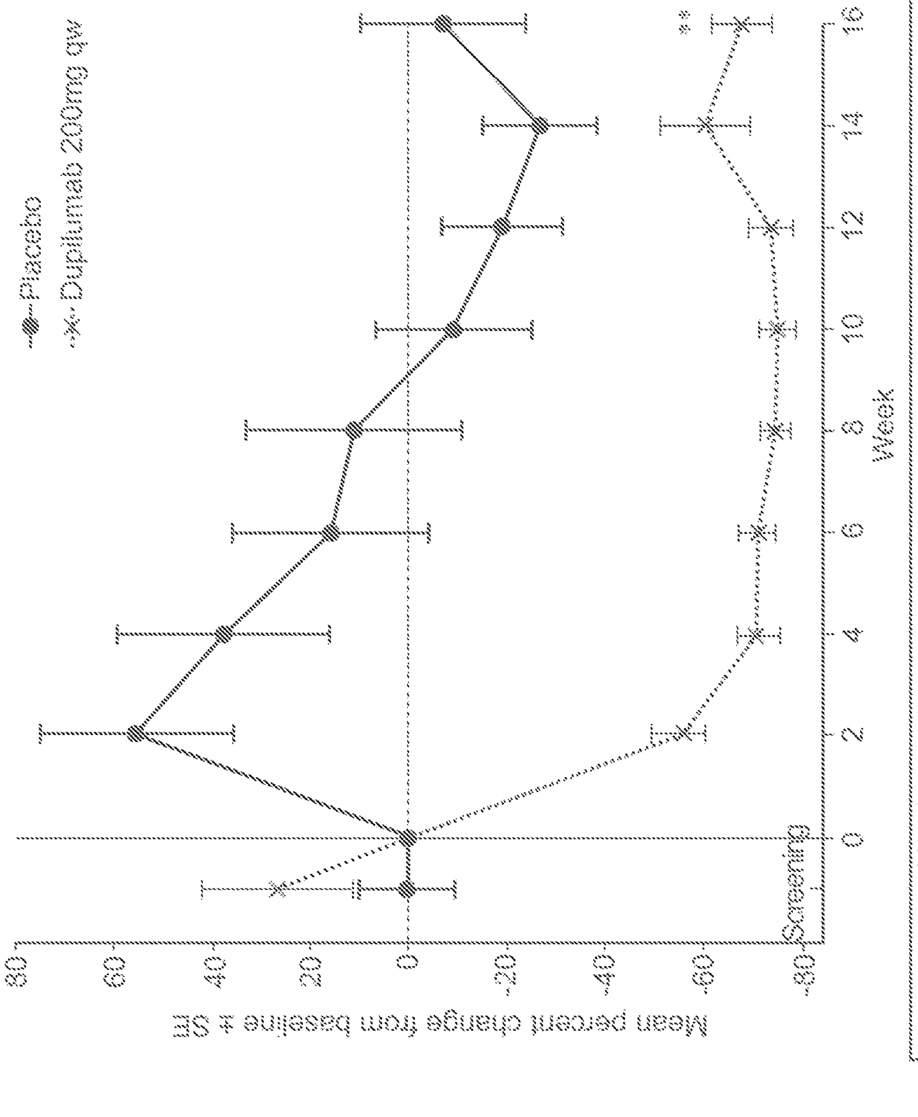
FIG. 3 shows serum thymus and activation-regulated chemokine (TARC) levels from baseline to week 16 in the study described in Example 2. **P<0.001 vs placebo; DPL, dupilumab; PBO, placebo; qw, once weekly; SE, standard error.
Figure 4:
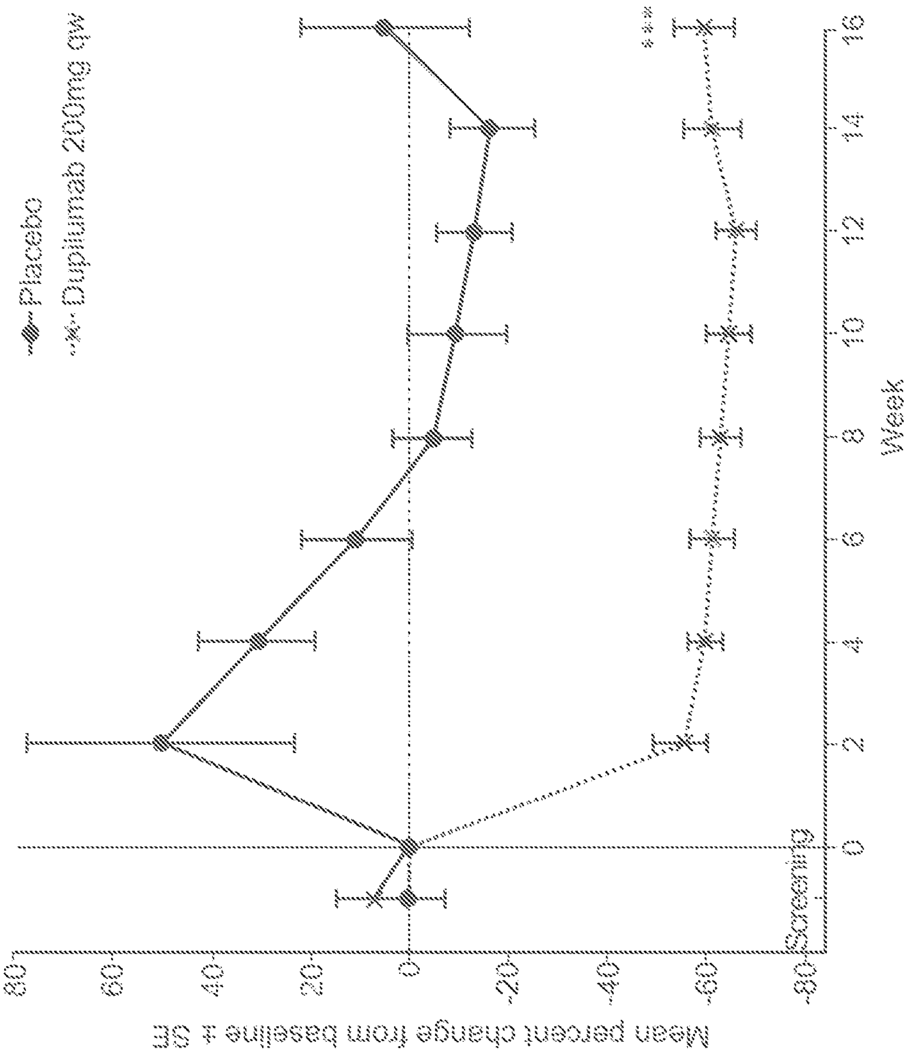
FIG. 4 shows serum pulmonary and activation-regulated chemokine (PARC) levels from baseline to week 16 in the study described in Example 2. ***P<0.0001 vs placebo; DPL, dupilumab; PBO, placebo; qw, once weekly; SE, standard error.
Figure 5:
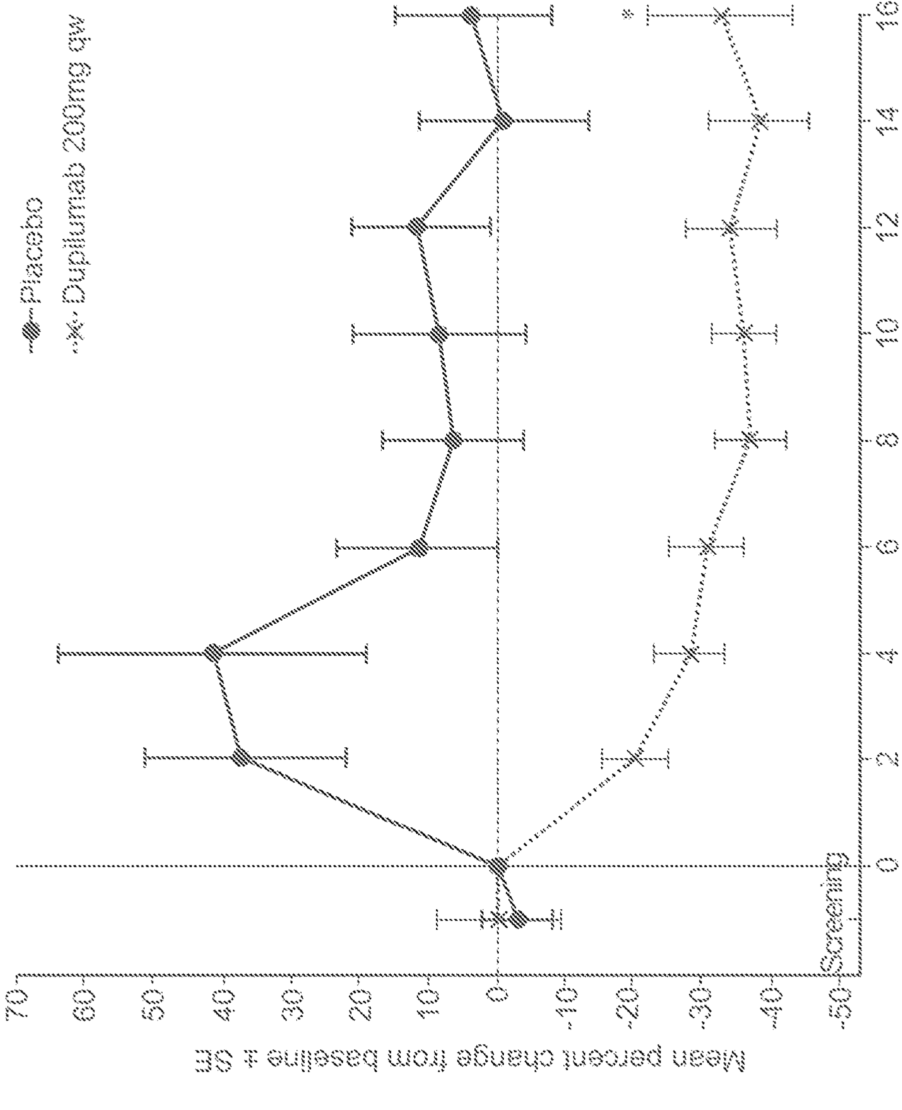
FIG. 5 shows serum periostin levels from baseline to week 16 in the study described in Example 2. *P<0.01 vs placebo; DPL, dupilumab; PBO, placebo; qw, once weekly; SE, standard error.
Figure 6:
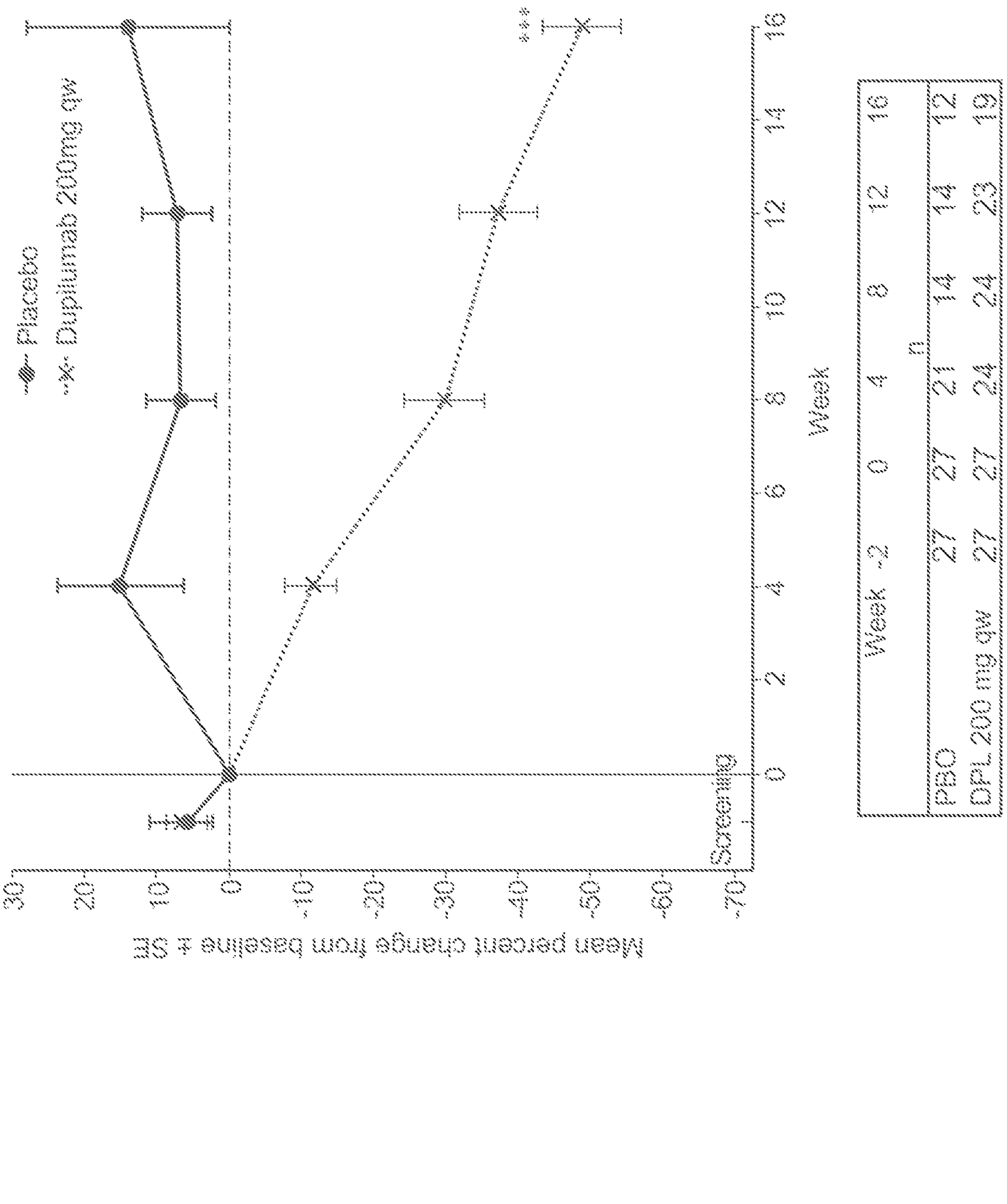
FIG. 6 shows serum total IgE levels from baseline to week 16 in the study described in Example 2. ***P<0.0001 vs placebo; DPL, dupilumab; PBO, placebo; qw, once weekly; SE, standard error.

TARC, thymus and activation-regulated chemokine;
SD, standard deviation;
PARC, pulmonary and activation-regulated chemokine Table 2 shows the baseline biomarker scores in both the treatment groups. Rapid and significant decreases in serum TARC, PARC and periostin (FIGS. 3-5) were observed with dupilumab treatment compared with placebo. Serum total IgE levels steadily declined during the treatment period, demonstrating a significant reduction at Week 16 in the dupilumab group compared with placebo (FIG. 6).

Mean and median decreases from baseline in antigen-specific IgEs, from week 1 through the end of the study (week 32) were noted for IgEs elicited against all allergen panels tested, which comprised Alder Grey, *Alternaria Tenuis*, Bermuda Grass, Silver Birch, Cat Dander, *Cladosporium*, Cockroach (German), *Dermatophagoides farinae*

(mite), Dog Dander, Elm, Johnson Grass, White Oak, Ragweed Short, Mugwort Sage, Timothy (*Phleum*), White Ash, *Staphylococcal enterotoxin* A, and *Staphylococcal enterotoxin* B. Dupilumab significantly suppressed a wide range of serum allergen-specific IgEs compared with placebo (FIG. 7; median baseline (IQR) and median percent change (IQR) from baseline to Week 16).

B. Study B

In "Study B", serum biomarkers were measured in samples from a clinical trial involving subjects with moderate-to-severe AD. Subjects with AD were randomized in a 1:1:1:1:1:1 ratio to receive 16 weeks of treatment with subcutaneous placebo weekly; or dupilumab 100 mg every 4 weeks (q4w), 300 mg q4w, 200 mg every 2 weeks (q2w), 300 mg q2w, or 300 mg weekly (qw). Patients in the 300 mg dose groups received a loading dose of 600 mg, whilst patients in the 200 and 100 mg dose groups received 400 mg on Day 1. The 16-week treatment period was followed by a 16-week safety follow-up (32-week total study period). AD-associated serum biomarkers such as thymus and activation-regulated chemokine (TARC), pulmonary and activity-regulated chemokine (PARC), periostin, lactate dehydrogenase, eosinophil, total IgE, and antigen-specific IgE are described in US Patent Application Publication No. US2014/0072583 (incorporated by reference in its entirety).

Serum biomarkers that were measured at various time points between screening and Week 32 included: Serum levels of TARC (Human CCL17/TARC Quantikine ELISA kit; R&D Systems, Minneapolis, MN, USA); Serum periostin (Human Periostin/OSF-2 DuoSet 15 Plate; R&D Systems); LDH (Roche Modular and Cobas Analyzers (Roche Diagnostics, Indianapolis, IN, USA); Eosinophil counts determined as part of the differential cell count; and Total IgE and antigen-specific IgEs in serum (measured by ImmunoCap assay (ImmunoCAPR Fluorescent Enzyme Immunoassay; Thermo Scientific, Phadia AB, Uppsala, Sweden).

For allergen-specific IgE, the lower limit of quantitation LLQ) was 0.10 kU/L; a level ≥0.35 kU/L was considered evidence of allergen sensitization.

Mean percent changes in serum biomarkers TARC, periostin and LDH, and median percent changes in total IgE and allergen-specific IgEs were compared at Week 16 for each of the dupilumab dosing regimens versus placebo using an analysis of covariance with the baseline value as a covariate.

Reductions from baseline to Week 16 with dupilumab vs placebo were observed in multiple antigen-specific IgEs in serum, including those specific for *S. aureus* enterotoxins (FIGS. 8 and 9).

Example 3: *Staphylococcus aureus* Skin Colonization

Skin microbial colonization analysis was conducted on samples taken from subjects who participated in a clinical trial of dupilumab. Subjects with moderate-to-severe atopic dermatitis (AD) were administered 16 weekly doses of either dupilumab (200 mg) or placebo; patients on dupilumab received a loading dose of 400 mg on day 1. *S. aureus* colonization and infection was determined on AD lesional and non-lesional skin between screening and Week 32. Skin swabs (pre-moistened with Tris-EDTA buffer) were collected from pre-measured skin areas (~10 cm×10 cm) and tested for the presence of *S. aureus*. Bacterial cells contained in the swab were lysed, and total genomic DNA purified. The abundance of *S. aureus*-specific femA DNA from total bacterial genomic DNA was determined using quantitative real-time PCR (qPCR). The relative colony-forming units (rCFU) of *S. aureus* was determined using a standard curve generated with genomic DNA from known CFU of *S. aureus*. *S. aureus* abundance was reported as median (interquartile range [IQR]) percent change from baseline. Data were set to missing after rescue medication. Variables were not adjusted for multiplicity and thus nominal p values are provided.

Figure 10:
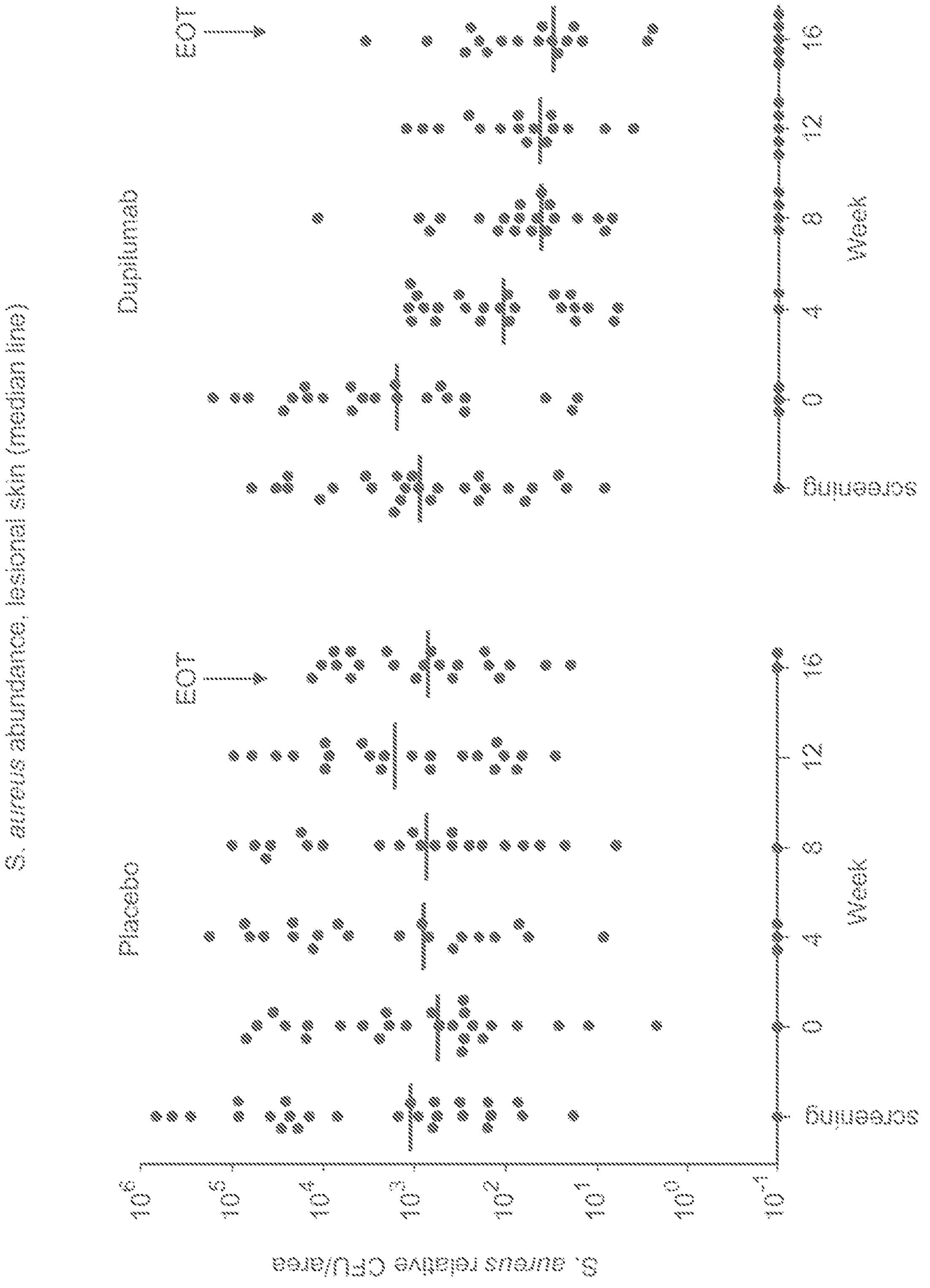
FIG. 10 shows *Staphylococcus aureus* abundance in lesional skin of patients with atopic dermatitis in the study in Example 3.

Dupilumab significantly reduced *S. aureus* abundance in AD lesional skin (median % change from baseline to Week 16 compared with placebo [P=0.0125; Table 3]), and an overall reduction from baseline was observed at Week 16 in median *S. aureus* abundance compared with placebo (FIG. 10).

TABLE 3

*S. aureus* abundance in AD lesional and non-lesional skin after 16-weeks treatment

| | Placebo qw (n = 27) | | Dupilumab 200 mg qw (n = 27) | |
|---|---|---|---|---|
| | Baseline median (Q1, Q3), rCFU/area | Median % change (Q1, Q3), rCFU/area | Baseline median (Q1, Q3), rCFU/area | Median % change (Q1, Q3), rCFU/area |
| AD lesional skin | 1289 (239.0, 16149.0) | −49 (−87.7, 635.8) | 1630 (287.3, 15442.5) | −99 (−99.9, −94.1)* |
| AD non-lesional skin | 166 (101.2, 4755.6) | −11 (−90.7, 1063.4) | 374 (84.8, 3146.4) | −89 (−97.5, −21.6) |

Figure 11:
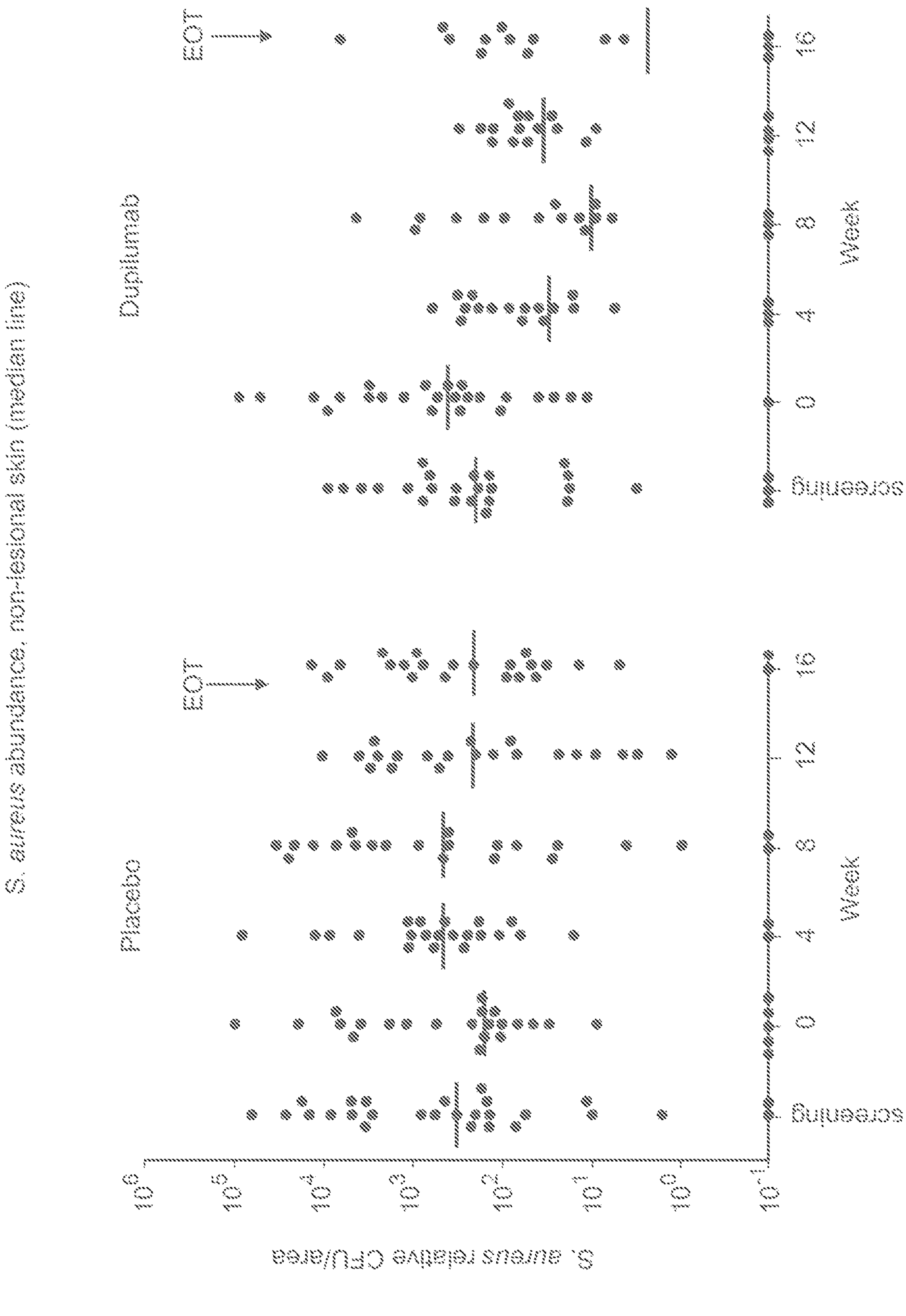
FIG. 11 shows *S. aureus* abundance in non-lesional skin of patients with atopic dermatitis in the study in Example 3.

*P < 0.05 vs placebo;
Q1, lower quartile of interquartile range;
Q3, upper quartile of interquartile range;
rCFU, relative colony forming units;
qw, once weekly In non-lesional AD skin, the dupilumab group demonstrated a numerically greater reduction in *S. aureus* abundance compared with placebo (median % change from baseline to Week 16 [Table 3; P=0.9865]), and an overall median reduction from baseline at Week 16 compared with placebo (FIG. 11).

Example 4: Dupilumab Improves Symptoms of Perennial Allergic Rhinitis (PAR) in Uncontrolled Persistent Asthma Patients with Comorbid PAR Dupilumab, an anti-interleukin (IL)-4 receptor-α monoclonal antibody, inhibits IL-4 and IL-13 signaling, key drivers of type 2 inflammation. In a pivotal, phase 2b study (NCT01854047), dupilumab improved forced expiratory volume in 1 second, reduced severe asthma exacerbations, improved quality-of-life, and was generally well tolerated in patients with uncontrolled persistent asthma despite use of medium-to-high-dose inhaled corticosteroids plus long-acting $R_2$-agonists (ICS+LABA). This post-hoc analysis examines the effect of dupilumab on the Sino-Nasal Outcome Test (SNOT-22) total score as well as individual items typically associated with allergic rhinitis (nasal blockage, runny nose, sneezing, and post-nasal discharge) in patients with perennial allergic rhinitis (PAR), a common comorbidity of asthma. PAR was defined by the presence of specific IgE 0.35 Ku/L against perennial antigens (*Aspergillus fumigatus*, cat dander, *D. farinae, D. pteronyssinus*, dog dander, German cockroach, or Oriental Cockroach) at study entry. Due to possible confounding effects, patients with comorbid nasal polyposis were excluded from the analysis. Data are reported for the intent-to-treat population who received placebo and either of the dupilumab regimens 200 or 300 mg every 2 weeks [q2w] currently under investigation in phase 3 (NCT02414854). Endpoints were change from baseline to Week 24 in SNOT-22 total score as well as the individual items, post-nasal discharge, nasal blockage, runny nose, and sneezing. Of 392 patients receiving dupilumab (200 or 300 mg q2w) or placebo, 241 (61%) had PAR. In PAR patients, dupilumab 300 mg q2w showed a significant improvement on SNOT-22 total score (LS mean difference −5.98 [95% CI, −10.45 to −1.51], P=0.009 vs. placebo) and all 4 allergic rhinitis-associated symptoms as defined above relative to placebo (nasal blockage: −0.60 [95% CI, −0.96 to −0.25]; runny nose: −0.67 [95% CI, −1.04 to −0.31]; sneezing: −0.55 [95% CI, −0.89 to −0.21]; and post-nasal discharge: −0.49 [95% CI, −0.83 to −0.16]; all P<0.01 vs. placebo); dupilumab 200 mg q2w showed a numerical, but not statistically significant decrease in SNOT-22 total score (~1.82 [95% CI, −6.46 to 2.83], P=0.443) as well as in the 4 allergic rhinitis-associated symptoms. No differences relative to placebo were observed in non-PAR patients on SNOT-22 total score and the 4 allergic rhinitis-associated symptoms. In conclusion, dupilumab 300 mg q2w significantly improves sinonasal symptoms in patients with uncontrolled persistent asthma and comorbid PAR.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of improving a symptom associated with allergic rhinitis in a subject, the method comprising subcutaneously administering a therapeutically effective amount of an interleukin-4-receptor (IL-4R) antagonist to the subject in need thereof, wherein the subject has asthma and has comorbid perennial allergic rhinitis;

wherein prior to treatment the subject has a serum allergen-specific IgE≥0.35 kU/L against an allergen that is an aeroallergen;

wherein the IL-4R antagonist is dupilumab; and wherein the subject achieves (i) an improvement in nasal blockage, (ii) an improvement in runny nose, (iii) an improvement in sneezing, and/or (iv) an improvement in post-nasal discharge.

2. The method of claim 1, wherein the subject achieves each of (i) an improvement in nasal blockage, (ii) an improvement in runny nose, (iii) an improvement in sneezing, and (iv) an improvement in post-nasal discharge.

3. The method of claim 1, wherein prior to treatment the subject has a serum allergen-specific IoE≥0.35 kU/L against one or more of *Aspergillus fumigatus*, cat dander, *Dermatophagoides farinae, Dermatophagoides pteronyssinus*, dog dander, and German cockroach.

4. The method of claim 1, wherein the IL-4R antagonist is administered at a dose of about 75 mg to about 600 mg.

5. The method of claim 4, wherein the IL-4R antagonist is administered at a dose of about 300 mg once every two weeks (Q2W).

6. The method of claim 4, wherein the IL-4R antagonist is administered at a dose of about 200 mg Q2W.

7. The method of claim 5, wherein the IL-4R antagonist is administered at a dose of 300 mg Q2W for at least 24 weeks.

8. The method of claim 6, wherein the IL-4R antagonist is administered at a dose of 200 mg Q2W for at least 24 weeks.

9. The method of claim 1, wherein the IL-4R antagonist is administered at an initial dose of about 600 mg followed by subsequent doses of about 300 mg, wherein each subsequent dose is administered one week or two weeks after the immediately preceding dose.

10. The method of claim 1, wherein the IL-4R antagonist is administered at an initial dose of about 400 mg followed by subsequent doses of about 200 mg, wherein each subsequent dose is administered one week or two weeks after the immediately preceding dose.

11. The method of claim 9, wherein the IL-4R antagonist is administered at an initial dose of 600 mg followed by secondary doses of 300 mg, wherein each subsequent dose is administered two weeks after the immediately preceding dose (Q2W).

12. The method of claim 11, wherein the IL-4R antagonist is administered for at least 24 weeks.

13. The method of claim 10, wherein the IL-4R antagonist is administered at an initial dose of 400 mg followed by secondary doses of 200 mg, wherein each subsequent dose is administered two weeks after the immediately preceding dose (Q2W).

14. The method of claim 13, wherein the IL-4R antagonist is administered for at least 24 weeks.

15. The method of claim 11, wherein the IL-4R antagonist is contained in an autoinjector.

16. The method of claim 11, wherein the IL-4R antagonist is contained in a pen delivery device.

17. The method of claim 13, wherein the IL-4R antagonist is contained in an autoinjector.

18. The method of claim 13, wherein the IL-4R antagonist is contained in a pen delivery device.

* * * * *